United States Patent
Cook et al.

(10) Patent No.: US 6,623,500 B1
(45) Date of Patent: Sep. 23, 2003

(54) RING CONTACT FOR ROTATABLE CONNECTION OF SWITCH ASSEMBLY FOR USE IN A SURGICAL SYSTEM

(75) Inventors: Robert G. Cook, Mason, OH (US); Richard F. Schwemberger, Cincinnati, OH (US); Ashvani K. Madan, Mason, OH (US); William T. Donofrio, Cincinnati, OH (US); Robert P. Gill, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 81 days.

(21) Appl. No.: 09/693,549

(22) Filed: Oct. 20, 2000

(51) Int. Cl.⁷ .............................................. A61B 17/32
(52) U.S. Cl. ...................................... 606/170; 702/106
(58) Field of Search ................................ 606/169, 170, 606/171; 604/22, 164

(56) References Cited

U.S. PATENT DOCUMENTS

| | | | | |
|---|---|---|---|---|
| 2,917,691 A | | 12/1959 | DePrisco et al. ............ 318/118 |
| 4,428,748 A | * | 1/1984 | Peyman et al. ............. 433/119 |
| 5,001,649 A | | 3/1991 | Lo et al. ..................... 364/484 |
| 5,026,387 A | * | 6/1991 | Thomas ................. 310/316.01 |
| 5,112,300 A | | 5/1992 | Ureche ......................... 604/22 |
| 5,180,363 A | | 1/1993 | Idemoto et al. .............. 202/32 |
| 5,400,267 A | | 3/1995 | Denen et al. ................ 364/552 |
| 5,425,704 A | | 6/1995 | Sakurai et al. ................ 604/22 |
| 5,449,370 A | | 9/1995 | Vaitekunas ................... 606/169 |
| 5,630,420 A | | 5/1997 | Vaitekunas ............. 128/662.03 |
| 5,707,369 A | | 1/1998 | Vaitekunas et al. ........... 606/31 |
| 5,879,364 A | * | 3/1999 | Bromfield et al. ............. 604/22 |
| 5,935,143 A | * | 8/1999 | Hood ............................ 604/22 |
| 5,951,581 A | * | 9/1999 | Saadat et al. .................. 604/22 |
| 5,968,007 A | | 10/1999 | Simon et al. ................... 604/22 |
| 6,017,354 A | | 1/2000 | Culp et al. .................... 606/170 |
| 6,019,775 A | | 2/2000 | Sakurai ....................... 606/169 |
| 6,066,135 A | | 5/2000 | Honda .......................... 606/39 |
| 6,090,123 A | | 7/2000 | Culp et al. .................... 606/180 |

FOREIGN PATENT DOCUMENTS

JP 175926 6/2000 ........... A61B/17/22

* cited by examiner

Primary Examiner—Michael J. Milano
Assistant Examiner—Victor Nguyen
(74) Attorney, Agent, or Firm—Darby & Darby

(57) ABSTRACT

The present invention provides a surgical handpiece having a switch end cap detachably and rotatably connected to the handpiece body. A surgical instrument is inserted within the handpiece body so that a portion thereof extends beyond the handpiece body and is actuated to perform a surgical operation. The switch end cap includes a switch mechanism having one or more switch button members for selectively signaling the level of power to be delivered to the handpiece from a power source. According to one aspect of the present invention, the switch mechanism within the switch end cap is electrically connected to the handpiece body in such a manner that permits the switch end cap to be freely rotated about the handpiece body, while still maintaining the electrical connection therebetween. This is accomplished by having conductive finger members and complementary conductive members provide the electrical connection between the switch end cap and the handpiece body. This permits a user to position the switch end cap in a desired location relative to the handpiece body and the instrument.

27 Claims, 13 Drawing Sheets

RING CONTACT FOR ROTATABLE CONNECTION OF SWITCH ASSEMBLY FOR USE IN A SURGICAL SYSTEM

BACKGROUND OF THE INVENTION

This invention relates to ultrasonic surgical systems and, more particularly, to an improved apparatus for facilitating the performance of surgical procedures such as simultaneous soft tissue dissection and cauterization of large and small blood vessels through the use of a precisely controlled ultrasonically vibrating instrument, such as a blade or scalpel.

It is known that electric scalpels and lasers can be used as surgical instruments to perform the dual function of simultaneously effecting the incision and hemostatis of soft tissue by cauterizing tissues and blood vessels. However, such instruments employ very high temperatures to achieve coagulation, causing vaporization and fumes as well as splattering, which increases the risk of spreading infectious diseases to operating room personnel. Additionally, the use of such instruments often results in relatively wide zones of thermal tissue damage.

Cutting and cauterizing of tissue by means of surgical blades vibrated at high speeds by ultrasonic drive mechanisms is also well known. In such systems, an ultrasonic generator is provided which produces an electrical signal of a particular voltage, current and frequency, e.g., 55,500 cycles per second. The generator is connected by a cable to a handpiece, which contains piezoceramic elements forming an ultrasonic transducer. In response to a switch on the handpiece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The blade is often non-symmetrical in shape and, during the surgical procedure, the physician manipulates the handpiece to cause the blade to contact the tissue to be treated. Because the switch which control operation of the blade is disposed on the handpiece, the location of the switch may at times prevent the physician from contacting tissue with the desired orientation of the blade because the relative position between the switch and the blade may prevent or render it difficult for the physician to manipulate the blade to the proper position while still being able to activate the switch with his/her fingers.

Thus, there is a need for a handpiece and switch assembly which will permit the physician to freely access tissue and operate thereon without having to worry about the relative position between the switch and the blade.

SUMMARY OF THE INVENTION

The present invention is directed towards a surgical instrument and, more particularly, to a surgical handpiece having a switch end cap detachably and rotatably connected to a handpiece body. Preferably, the surgical instrument comprises an ultrasonic surgical instrument which uses ultrasonic vibrations to perform a surgical operation. An instrument, such as a blade, e.g., a scalpel blade, is inserted and secured within the handpiece body so that a portion of the blade extends beyond the handpiece body for contacting tissue and the like. The switch end cap includes a switch mechanism having one or more switch button members for selectively signaling the level of power delivered to the handpiece from a power source, e.g., an external ultrasonic generator. Preferably, the switch mechanism includes at least two settings, namely a low power setting and a high power setting. When the high power setting is selected, the blade is ultrasonically vibrated at an elevated level and when the low power setting is selected, the blade is ultrasonically vibrated at a reduced level. The switch mechanism is actuated by pressing a portion of one switch button member depending upon whether high or low power is desired for the particular application.

In one exemplary embodiment, the handpiece body is coupled to the power source by a power cable which extends from one end of the handpiece body. The components for producing the ultrasonic vibrations include, but are not limited to, a transducer and a horn which is connected to the transducer at one end and to the blade at an opposite end. The blade preferably is easily attachable/detachable from the horn to permit the blade to be easily cleaned, serviced or replaced. The horn extends along a longitudinal axis of the handpiece body and at least a portion of the horn extends beyond the end of the handpiece body where it is coupled to the blade. This end of the handpiece body is configured to receive one end of the switch end cap in a releasably engaged manner. It will also be appreciated that the handpiece body and switch end cap may be semi-permanently or permanently connected to one another while still being rotatable relative to one another.

According to one aspect of the present invention, the handpiece body and the switch mechanism disposed within the switch end cap are electrically connected to one another in such a manner that permits the switch end cap may be freely rotated about the handpiece body while the electrical connection is maintained. This permits a user, e.g. a surgeon, to rotate the switch end cap during operation of the handpiece in order to position the switch end cap in an optimum position relative to the blade. Because the blade has a generally non-symmetrical nature, the surgeon may prefer to alter the relative position of the switch end cap with respect to the blade in order to conveniently contact tissue. The present invention provides such a feature and permits the surgeon to tailor the specific location of the switch end cap for and during a specific surgical operation.

In yet another aspect of the present invention, a seal member is disposed within the handpiece body and is preferably formed of an elastic material which intimately engages a sheath portion of the blade to form a seal therebetween. The seal member prevents unwanted foreign material from entering the inside of the switch end cap and making contact with the switch mechanism or other internal components. In a preferred embodiment, the seal member comprises an annular seal member which is concentrically disposed relative to the sheath of the blade to form the seal therebetween. The sheath member is also preferably formed of an elastic material which permits an effective seal to be formed.

Other features and advantages of the present invention will be apparent from the following detailed description when read in conjunction with the accompanying drawings.

BRIEF DESCRIPTION OF THE DRAWINGS

The foregoing and other features of the present invention will be more readily apparent from the following detailed description and drawings of an illustrative embodiment of the invention in which.

DESCRIPTION OF ILLUSTRATIVE EXEMPLARY EMBODIMENTS

Figure 1:
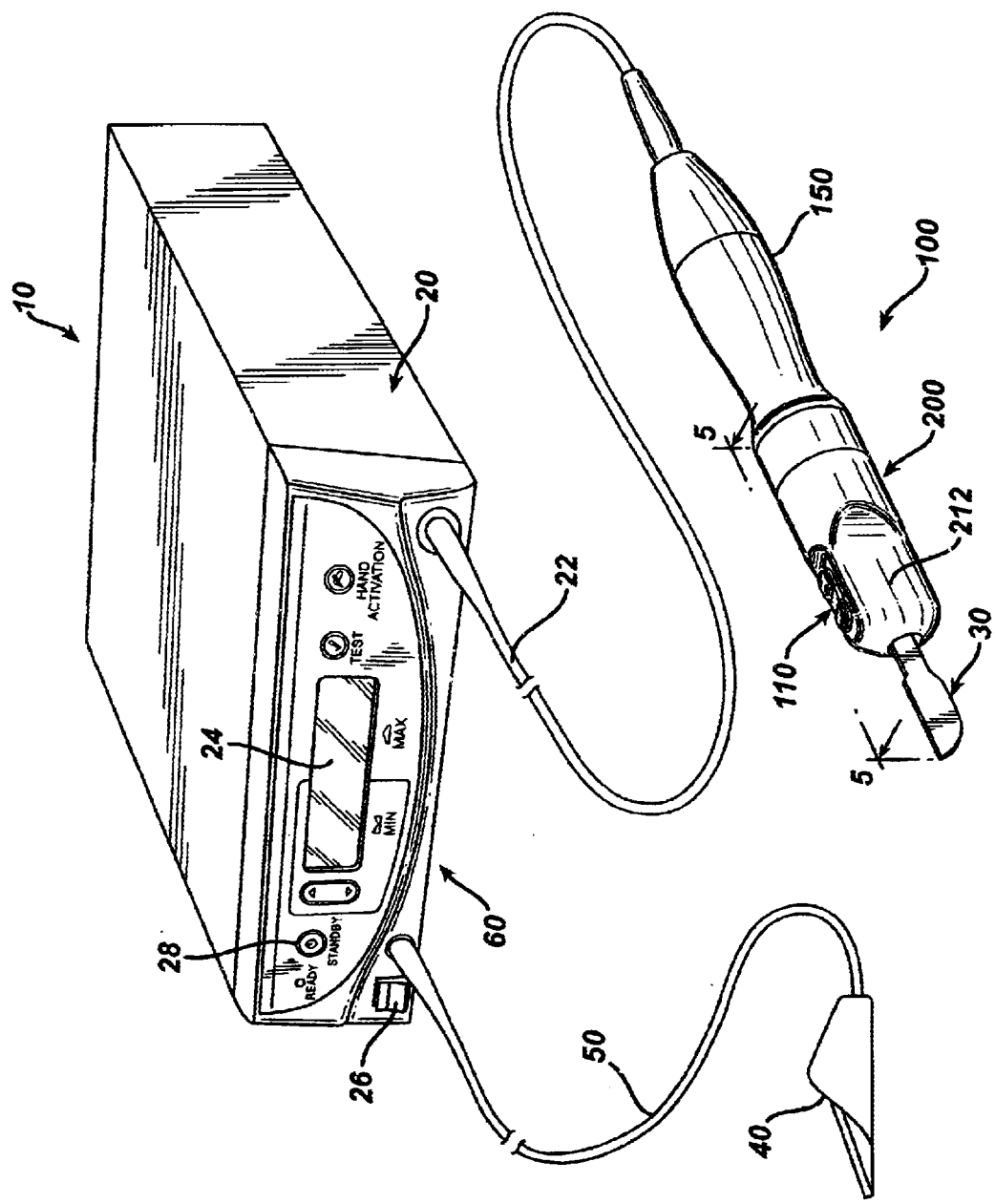
FIG. 1 is an illustration of a console for an ultrasonic surgical cutting and hemostatis system, as well as a handpiece and foot switch in accordance with an exemplary embodiment of the present invention.

Referring first to FIG. 1 in which an ultrasonic surgical cutting and hemostatis system according to the present invention is illustrated and generally indicated at 10. The system 10 includes a console or housing 20 for containing an ultrasonic generator (not shown) and a control system located within the console 20 which forms a part of the system 10. A first cable 22 connects the console 20 to a handpiece 100 and serves to provide an electrical connection therebetween. The first cable 22 includes a first set of wires (not shown) which permit electrical energy, i.e., drive current, to be sent from the console 20 to the handpiece 100 where it imparts ultrasonic longitudinal movement to a surgical instrument 30. According to the present invention, the surgical instrument 30 is preferably a sharp scalpel blade or shear. This instrument 30 can be used for simultaneous dissection and cauterization of tissue.

The supply of ultrasonic current to the handpiece 100 is controlled by a switch mechanism 110 disposed within the handpiece 100. As will be described in greater detail hereinafter, the switch mechanism 110 is connected to the console 20, more specifically the generator thereof, by one or more wires (not shown) of the first cable 22. The generator may also be optionally and further controlled by a foot switch 40 which is connected to the console 20 by a second cable 50. Thus, in use, a surgeon may apply an ultrasonic electrical signal to the handpiece 100, causing the instrument 30 to vibrate longitudinally at an ultrasonic frequency, by operating the switch mechanism 110 on the handpiece 100 or the foot switch 40. The switch mechanism 110 is activated by the hand of the surgeon and the foot switch 40 is activated by the surgeon's foot.

The console 20 also includes a liquid crystal display device 24, which can be used for indicating the selected cutting power level in various means, such as percentage of maximum cutting power or numerical power levels associated with the cutting power. The liquid crystal display device 20 can also be utilized to display other parameters of the system. A power switch 26 and power "on" indicator 28 are also provided on the console 20 to permit the user to further control the operation of system 10. Additional buttons and control switches, generally indicated at 60, control various other functions of the system 10 and may be located on the front panel of the console 20.

When the power is applied to the ultrasonic handpiece 100 by operation of either switch mechanism 110 or switch 40, the surgical scalpel or instrument 30 is caused to vibrate longitudinally at approximately 55.5 KHz, and the amount of longitudinal movement will vary proportionately with the amount of driving power (current) applied, as adjustably selected by the user. When relatively high cutting power is applied, the instrument 30 is designed to move longitudinally in the range of about 40 to 100 microns at the ultrasonic vibrational rate. Such ultrasonic vibration of the instrument 30 will generate heat as the blade contacts tissue. This results because the acceleration of the instrument 30 through the tissue converts the mechanical energy of the moving instrument 30 to thermal energy in a very narrow and localized area. This localized heat causes a narrow zone of coagulation, which will reduce or eliminate bleeding in small vessels, such as those less than one millimeter in diameter. The cutting efficiency of the instrument 30, as well as the degree of hemostatis, will vary with the level of driving power applied, the cutting rate of the surgeon, the nature of the tissue type and the vascularity of the tissue. One exemplary ultrasonic surgical system is disclosed in commonly assigned U.S. patent application Ser. No. 09/693,621, entitled "Ultrasonic Surgical System", filed Oct. 20, 2000, which is incorporated herein by reference in its entirety.

Referring now to FIGS. 2–7, in which the handpiece 100 is illustrated in greater detail, the ultrasonic handpiece 100 houses a piezoelectric transducer, generally indicated at 120, for converting electrical energy to mechanical energy that results in longitudinal vibrational motion of the ends of the transducer. The transducer 120 is preferably in the form of a stack of ceramic piezoelectric elements with a motion null point between the end of the stack. A horn 130 is coupled to the transducer 120 on one side. Instrument 30 is fixed to a portion of the horn 130. As a result, the instrument 30 will vibrate in the longitudinal direction at the ultrasonic frequency rate of the transducer 120. The ends of the transducer 120 achieve maximum motion when the transducer 120 is driven with a current of 380 mA RMS at the transducer resonant frequency. This is merely a general overview of the operation of the handpiece 100 and one of skill in the art will appreciate how the specific components operate to accomplish the ultrasonic surgical action.

The parts of the handpiece 100 are designed such that the combination will oscillate at the same resonant frequency. In particular, the elements contained therein are tuned such that the resulting length of each element is one-half wavelength. Longitudinal back and forth motion is amplified as the diameter closer to the instrument 30 of the acoustical mounting horn 130 decreases. Thus, the horn 130, as well as the instrument 30, are shaped and diminished so as to amplify blade motion and provide harmonic vibration in resonance with the rest of the acoustic system, which produces the maximum back and forth motion of the end of the acoustical mounting horn 130 close to the instrument 30.

The handpiece 100 includes a body 150 which contains internal operating components, such as but not limited to the transducer 120 and the horn 130. The body 150 is designed to mate with a switch end cap 200 (FIG. 2) which is rotatably coupled to the body 150, as will be described in greater detail hereinafter. Preferably, the switch end cap 200 is detachable connected to the body 150. The body 150 has a distal end 152 and an opposing proximal end 154 which attaches to one end of the cable 22. The body 150 may have any number of shapes and is designed so that a user may easily grip and comfortably hold the handpiece 100 in one's hand. Preferably, the body 150 is generally annular in shape and in the exemplary embodiment, the handpiece 100 has a design with multiple tapered sections permitting the user to grasp and rest a thumb and one or more fingers around the handpiece 100. In the illustrated embodiment, the body 150 is formed of a metal material; however, one will appreciate that the body 150 may be formed of a number of materials, including but not limited to plastic materials.

At the proximal end 154, an electrical adapter 156 is provided and is electrically connected to the cable 22 by means of one or more wires (not shown). The electrical adapter 156 is also electrically connected to other internal components of the handpiece 100 so that power may be selectively provided to the handpiece 100 using the switch mechanism 110, as will be described in greater detail hereinafter. The proximal end 154 is generally closed ended with the cable 22 being routed therethrough, while the distal end 152 is at least partially open ended. The horn 130 extends in the direction of the distal end 152 such that a distal tip 132 of the horn 130 extends beyond the distal end 152 of the handpiece 100. The distal tip 132 has a stud 156 or the like extending outwardly therefrom. Preferably, the stud 156 comprises a threaded stud and is designed to threadingly mate with the instrument 30 to secure the instrument 30 to the handpiece 100. The instrument 30 has a blade portion 32 (FIG. 5) with an insulative sheath 34 disposed about the blade portion 32. The blade portion 32 also has an exposed blade tip 36 which extends beyond the insulative sheath 34 so as to be available for contacting and cutting tissue and the like. The insulative sheath 34 is formed of any number of suitable insulative materials, and in one exemplary embodiment is formed of a plastics material.

Figure 2:
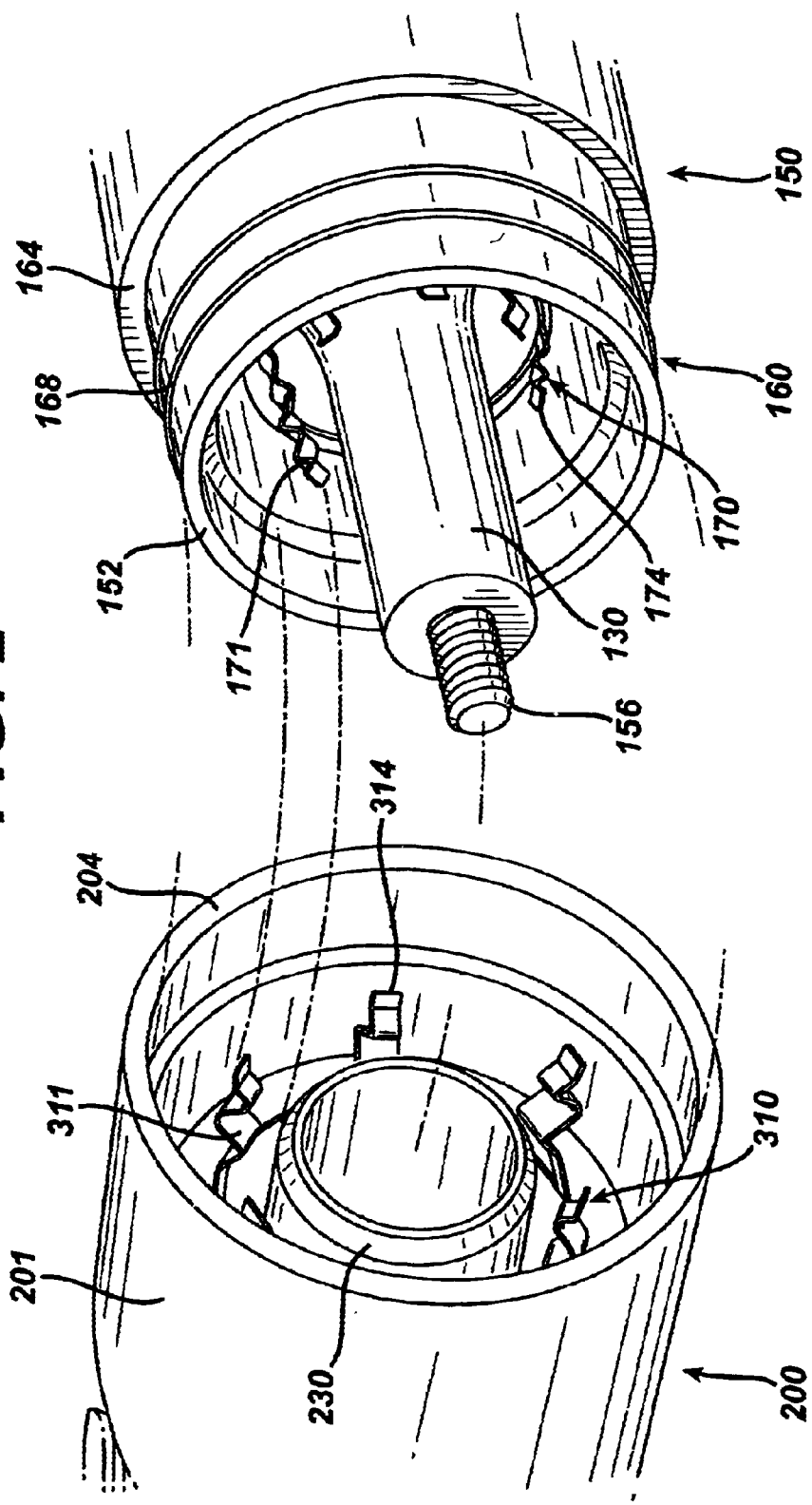
FIG. 2 is a fragmentary exploded perspective view of one exemplary handpiece and switch end cap.
Figure 3:
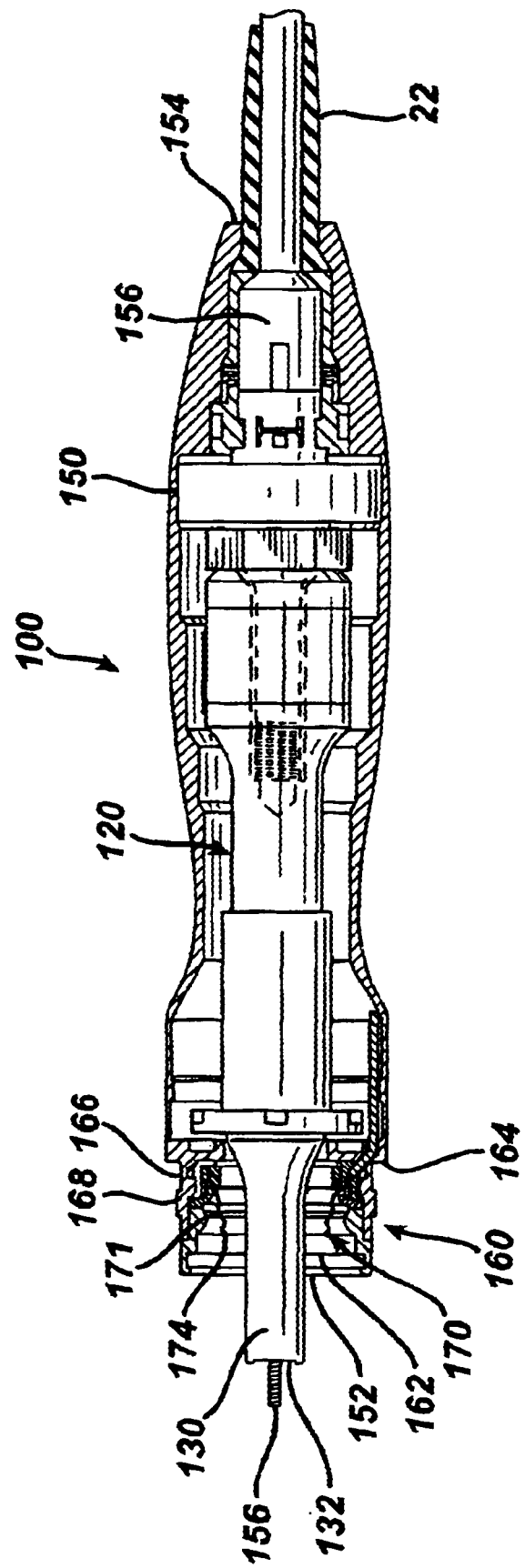
FIG. 3 is a longitudinal cross-sectional view of the handpiece.

At the distal end 152, the body 150 has a reduced diameter so as to form a flange member 160 (FIG. 3). The flange member 160 defines a cavity 162 through which the horn 130 extends. In the illustrated embodiment, the flange member 160 is annular in shape and extends to a location just before the distal tip 132 of the horn 130 so that a portion of the horn 130, including the distal tip 132, extends beyond the end of the flange member 160. A shoulder 164 is formed at the location where the flange member 160 extends from the remaining portion of the body 150. An outer surface 166 of the flange member 160 may include one or more ridges, generally indicated at 168, which extend annularly around the outer surface 166. In the illustrated embodiment shown in FIG. 2, there are two ridges 168 in the form of threads spaced apart from one another and, because of the annular shape of the outer surface 166, the ridges 168 comprise annular threads. It will be appreciated that the outer surface 166 is constructed so that it complementarily mates with the switch end cap 200.

Figure 7:
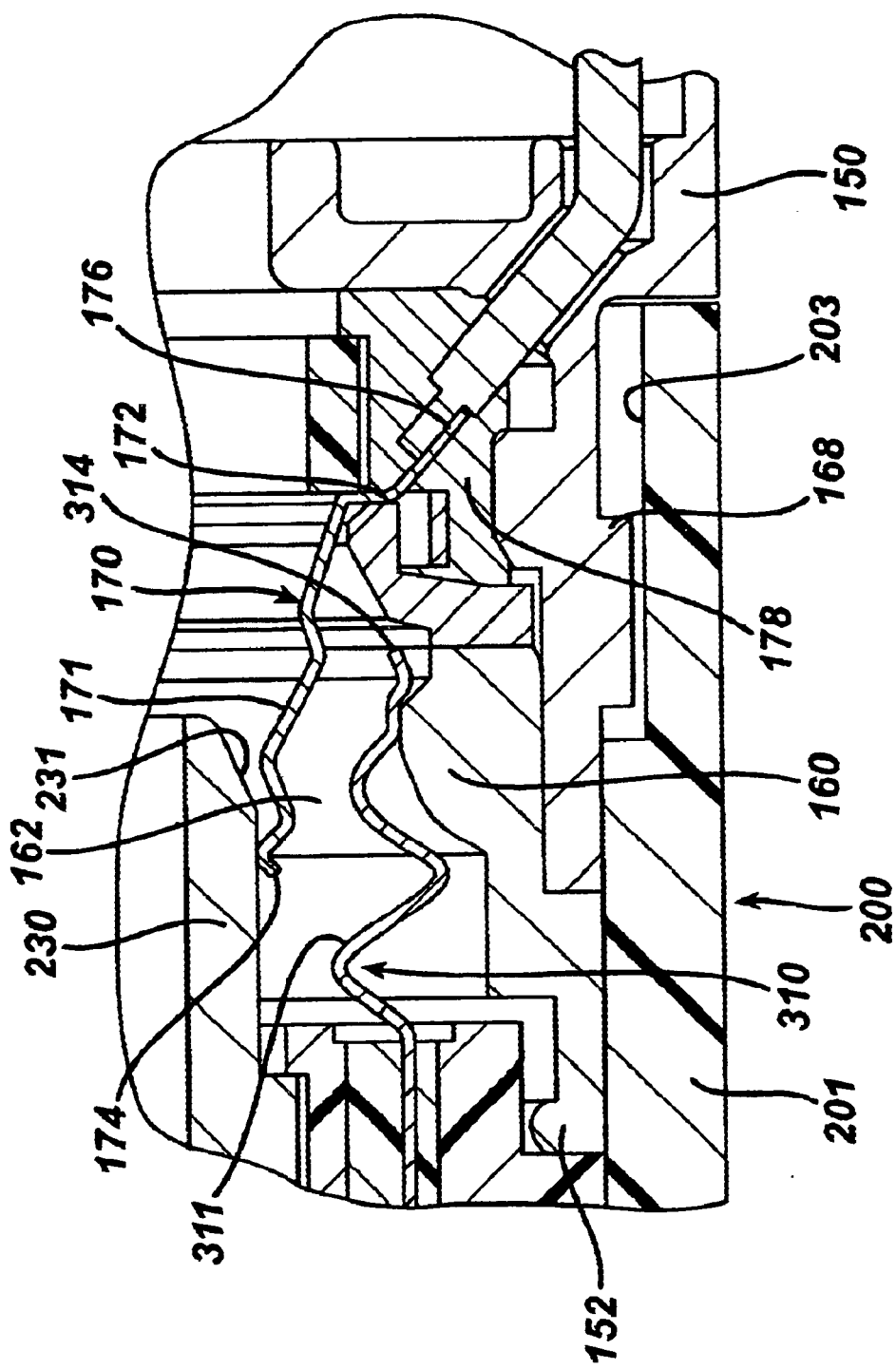
FIG. 7 is a fragmentary enlarged cross-sectional view of the electrical connection between the switch end cap and the handpiece body and taken along the line 7—7 of FIG. 4.

As best shown in FIGS. 2 and 7, the body 150 also includes a first conductive finger element 170 which is disposed about the horn 130 within cavity 162. In the exemplary embodiment, the first conductive finger element 170 is an annular ring-like member formed of a plurality of fingers 171 radially disposed about the horn 130. Each finger 171 of the conductive finger element 170 has a serially-connected first section 172 and a second section 174, which comprises a free end of the finger 171. The free second section 174 electrically engages another conductive member when the handpiece 100 is assembled, as will be described in greater detail hereinafter. The second section 174 is preferably bent in several locations so that it assumes a generally zig-zag shape and is resilient so that the fingers 171 may be bent outwardly under an applied force. It will be appreciated that instead of having a plurality of fingers 171, only a single finger 171 may be provided.

At the proximal end of the first section 172, each finger 171 connects to a first conductive base ring, generally indicated at 176, which provides a conductive path between all of the fingers 171. The first conductive base ring 176 is also used to properly locate and position the first conductive finger element 170 within the body 150 and more specifically, within the cavity 162. The first conductive base ring 176 is anchored within the body 150 and is electrically isolated from the conductive body 150 by using one or more spacers 178 which are disposed between the body 150 within the cavity 162 and the ring 176. Because of the annular shape of the body 150 and the horn 130, the one or more spacers 178 are generally in the form of insulative ring structures disposed between the fingers 171 and the conductive body 150. Typically, the one or more spacers 178 are formed of any number of suitable plastic materials or elastomeric materials. The first conductive finger element 170 is also spaced a sufficient distance from the horn 130, which is also formed of a conductive material, e.g., metal, so that the fingers 171 or other part of the element 170 do not make contact with the horn 130 during assembly of the handpiece 100. By disposing the one or more spacers 178 between the fingers 171 and the body 150, the spacer 178 serves to slightly urge the fingers 171 inwardly away from a conductive inner surface 151 of the body 150.

As previously mentioned with respect to FIG. 3, the cable 22 serves to provide power to the handpiece and accordingly, the first conductive finger element 170 is electrically connected to the electrical adapter 156 by means of one or more electrical wires (not shown) which extend along a length of the body 150 from the electrical adapter 156 to the first conductive finger element 170. It will also be appreciated and will be described in greater detail hereinafter, that the body 150 itself serves as an electrical pathway or wire because the body 150 is electrically connected to the cable 22.

Figure 4:
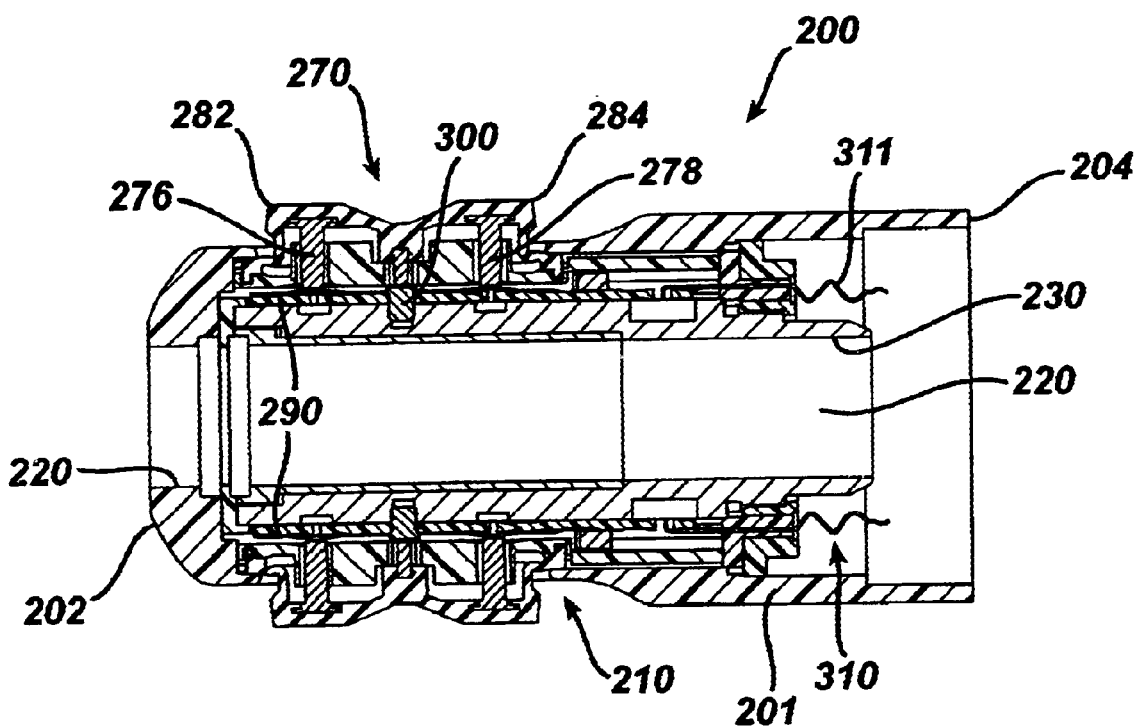
FIG. 4 is a longitudinal cross-sectional view of the switch end cap.

As best shown in FIGS. 4–7, the switch end cap 200 which mates with the body 150 so that the switch end cap 200 may freely rotate about the handpiece body 150 during operation of the handpiece 100. The switch end cap 200 is formed of an outer shell 201 having a distal end 202 and an opposing proximal end 204 with the proximal end 204 of the switch end cap 200 receiving and mating with the distal end 152 of the body 150 (FIG. 4). The shell 201 has an outer surface 206 (FIG. 7) which is contoured to be gripped and held by a user during operation of the handpiece 100. The proximal end 204 of the shell 201 is generally annular in nature and the exemplary shell 201 slightly tapers inwardly to form a switch section 210 close to the distal end 202. This slight taper forms finger shaped recessed portions which permit the fingers of a user to easily grip and hold the shell 201 as during coupling of the switch end cap 200 to the body 150 or during rotational movement of the switch end cap 200 relative to the body 150.

Figure 6:
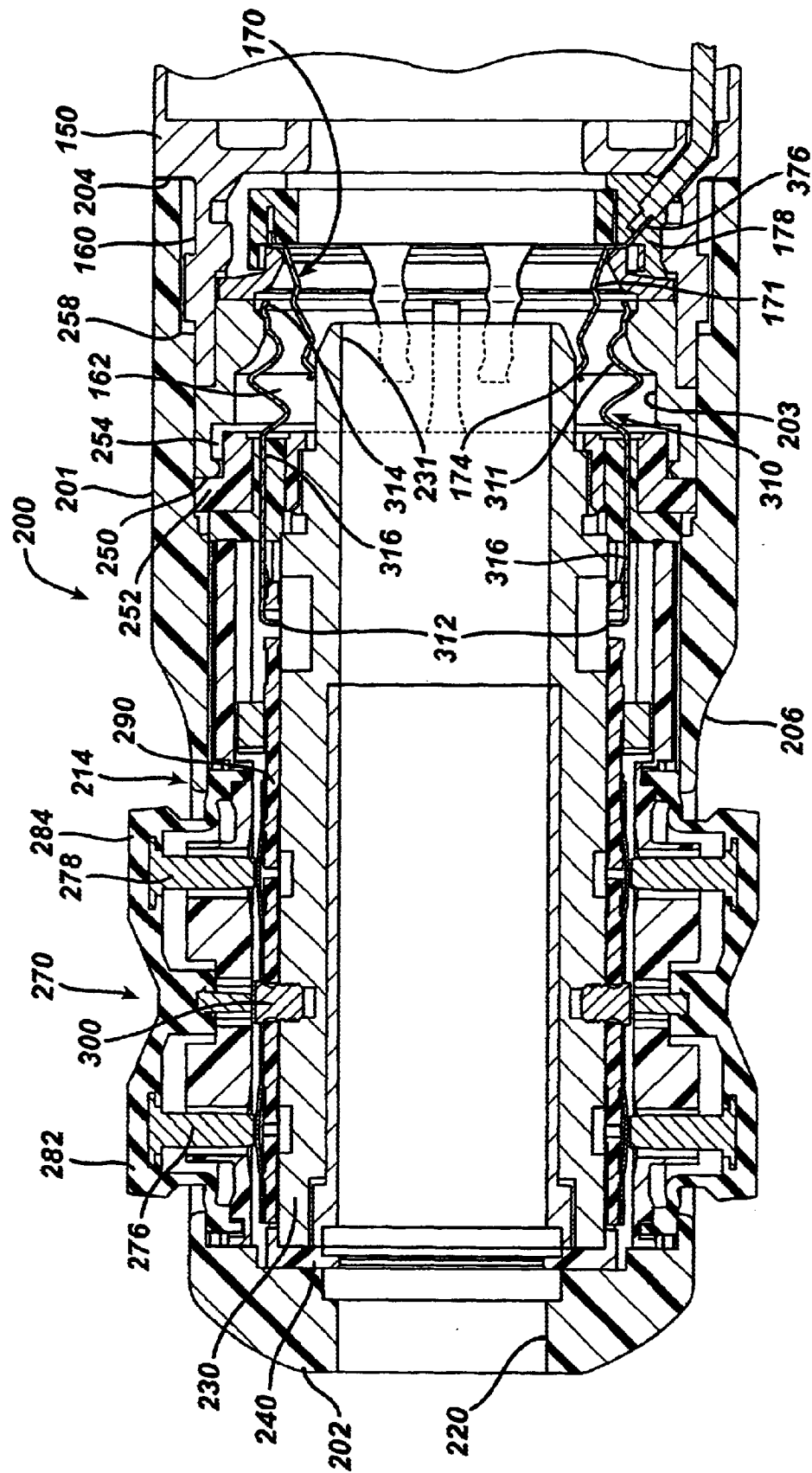
FIG. 6 is an enlarged cross-sectional view showing the switch end cap with a portion of the outer surface broken away.

The switch section 210 is actually formed of a pair of opposing contoured finger sections, generally indicated at 212 (FIG. 1), and a pair of opposing recessed button sections, generally indicated at 214 (FIG. 6). Preferably each finger section 212 is formed about 180° apart from the other finger section 212 and one recessed button section 214 is formed about 180° apart from the other button section 214. The holding and rotational manipulation of the shell 201 is done by placing a thumb on one finger section 212 and a finger, i.e., the middle finger, in the other of the finger sections 212. This permits the index finger to rest upon one of the button sections 214. Each button section 214 is slightly tapered relative to the proximal end 204, while the taper to form the finger sections 212 is more pronounced to accommodate resting locations for the thumb and one or more fingers.

The outer shell 201 is at least partially open at both the distal end 202 and the proximal end 204 with a bore 220 extending therethrough (FIG. 4). The bore 220 is sized to receive a first conductive member 230 which is securely located within the switch end cap 200 by disposing the first conductive member 230 within the bore 220. In the exemplary embodiment, the first conductive member 230 comprises a cylindrical member formed of a suitable conductive material, such as a metal. The first conductive member 230 extends along a length of the outer shell 201 from a point near the distal end 202 to a point near the proximal end 204. Preferably, the diameter of the opening at the distal end 202 is about the same size as the diameter of the conductive member 230 and is axially aligned therewith so as to permit access to the inside of the conductive member 230 so that the instrument 30 may inserted therein and the inside of the conductive member 230 may be cleaned, etc.

Figure 5:
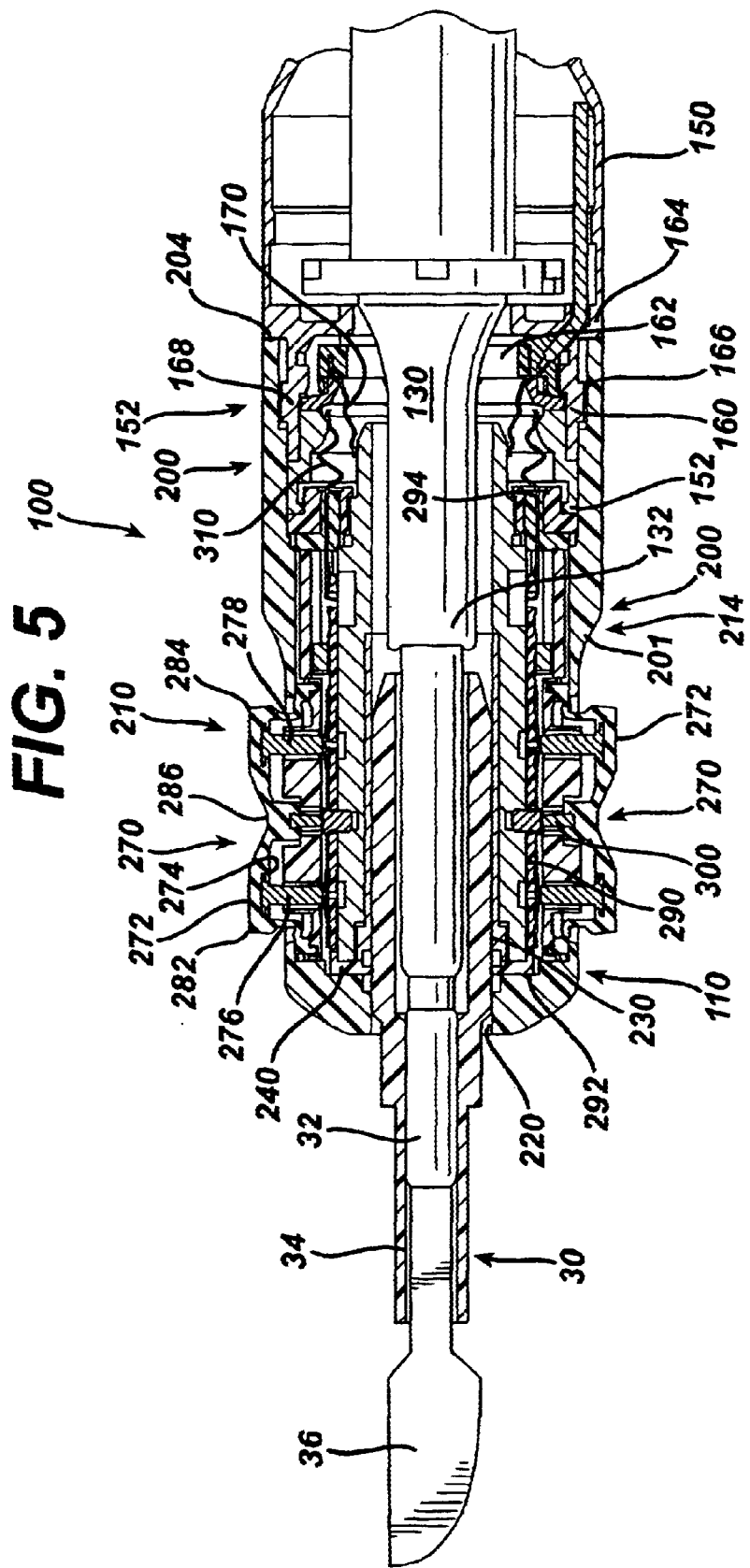
FIG. 5 is a cross-sectional view of the handpiece and switch end cap taken along the section line 5—5 of FIG. 1.

As best shown in FIGS. 5 and 6, at the distal end 202, a seal member 240 is disposed at the end of the conductive member 230. More specifically, the seal member 240 is retained in a groove formed in the shell 201 adjacent to the conductive member 230. The seal member 240 is preferably formed of an elastic material, preferably a plastics material, and more preferably is formed of silicon. As will be described in greater detail hereinafter, the seal member 240 is designed to prevent unwanted foreign matter from entering the inside of the conductive member 230. When the switch end cap 200 mates with the handpiece body 150, the instrument 30 extends through the conductive member 230 and exits through the opening formed at the distal end 202 of the switch end cap 200. Accordingly, the instrument 30 extends through the seal member 240. Due to the elastic nature of the seal member 240, the seal member 240 engages the sheath 34 of the instrument 30 to produce a seal therebetween. This seal prevents the unwanted foreign matter from entering through the opening formed at the distal end 202 of the shell 201 because any matter that might enter, during a surgical operation, is restricted by the seal member 240.

As best shown in FIG. 6, near the proximal end 204, the switch end cap 200 has an annular platform 250 formed thereat which is preferably concentric to the conductive member 230. The annular platform 250 has an opening formed at the center thereof because the bore 220 is formed through the annular platform 250 and more specifically, one end of the bore 220 begins at the annular platform 250. The annular platform 250 extends radially inwardly toward the proximal end 204 and away from another annular surface 252 which extends between the inner surface 203 of the shell 201. Because the annular platform 250 preferably has a diameter less than the diameter defined by the inner surface 203 of the outer shell 201, a gap 254 is formed between the annular platform 250 and an inner surface 203 of the shell 201. The annular platform 250 may thus be thought of as a spacer member. The conductive member 230 has a length such that a section of the conductive member 230 extends beyond the annular platform 250 into a cavity formed between the inner surface 203 of the shell 201 at the proximal end 204. The inner diameter of the shell 201 near the proximal end 204 may vary slightly due to one or more lip portions 258 being formed on the inner surface 203 of the shell 201. These one or more lip portions 258 serve to provide engaging surfaces for the handpiece 100 when the handpiece body 150 is coupled to the switch end cap 200.

As best shown in FIGS. 5 and 6, the switch end cap 200 also includes a pair of switch button members 270 which are detachably secured within the button sections 214 formed in the outer shell 201. Each switch button member 270 has an upper surface 272 and includes a flange 274 seating against a retainer 275 formed as part of the outer shell 201. The flange 274 seals with the retainer 275 so to prevent any foreign material and the like from entering the electronic switch components of the switch mechanism 110. The retainer 275 is preferably attached to the outer shell 201 by conventional techniques, including a snap-fit arrangement. First and second posts 276, 278, respectively, extend outwardly from the switch button member 270. The first and second posts 276, 278 are spaced apart from one another with a center traverse wall 280 being formed therebetween. The upper surface 272 includes a first raised section 282 and a second raised section 284 spaced therefrom with a center recessed section 286 being formed therebetween. The upper surface 272 is thus slightly beveled as the switch button member 270 transitions from the center recessed section 286 to the first and second raised sections 282, 284. In the illustrated embodiment, the first post 276 is disposed generally below the first raised section 282 and the second post 278 is disposed generally below the second raised section 284 so that when a user presses downwardly upon the first raised section 282, the first post 276 is also directed downward. Similarly, when the user presses downwardly upon the second raised section 284, the second post 278 is directed downward.

The switch button members 270 are designed to act as a depressable switch button for selectively causing activation of the handpiece 100 as will be described in greater detail hereinafter. The switch button members 270 are formed of suitable materials, such as plastic materials, and preferably the switch button members 270 are formed of a resilient plastic material. In one exemplary embodiment, the switch button members 270 are formed of silicon which permits the members to be sufficiently resilient enough so that they may be fitted and secured within the button sections 214 and also provide an engagement surface for a finger or thumb during operation of the handpiece 100. In one aspect of the present invention, the contour of the switch button member 270 permits a fingertip to easily rest between the first and second raised sections 282, 284. In other words, the finger tip seats and rests within the center recessed section 286 without actuating the switch mechanism 110. Because the switch button members 270 are disposed within the button sections 214, the switch button members 270 are spaced about 180° from one another. The recessed section 286 advantageously provides a location for the user to rest a finger during operation of the switch button member 270 without inadvertently activating the switch button member 270. This results because the recessed section 286 is above the pivot point of the switch button member 270.

The switch end cap 200 also includes a pair of printed circuit boards (PCBs) 290 which form a part of the electronic switch mechanism 110. The PCBs 290 are disposed within the outer shell 201 such that the PCBs 290 are disposed between the conductive member 230 and the switch button members 270. The PCBs 290 extend longitudinally relative to an axis extending through the bore 220 formed in the switch end cap 200. A distal end 292 of each PCB 290 is located near the distal end 202 of the switch end cap 200 and proximate to the seal member 240. The PCB 290 has a proximal end 294 opposite the distal end 292. It will be understood that instead of using PCBs 290, other suitable electronic components may be used, such as a flexible circuit component known as a "flexprint".

A pair of fasteners 300 serve to electrically connect the PCBs 290 to the conductive member 230. More specifically, one side of a switch circuit according to the present invention is defined by the conductive member 230 since the PCB 290 is electrically connected thereto. The pair of fasteners 300 extend through openings (not shown) formed in the PCBs 290 to provide the desired electrical connection between the PCBs 290 and the conductive member 230.

As shown in FIG. 5, the pair of fasteners 300 are positioned beneath the center traverse wall 280. Each button section 214 formed in the outer shell 201 contains openings formed therein and spaced apart from one another for receiving the first and second posts 276, 278 of the switch button member 270. The exemplary switch mechanism 110 is known as a rocker type switch mechanism and, according to the present invention, two switch button members 270 form, in part, the switch mechanism 110. Each switch button member 270 has two switch settings. For example, the first raised section 282 and the first post 276 are associated with a first switch setting and the second raised section 284 and the second post 278 are associated with a second switch setting. Preferably, the first switch setting of one switch button member 270 is the same as the first switch setting of the other switch button member 270 disposed about 180° therefrom. In one exemplary embodiment, the first switch setting is a maximum power setting and the second switch setting is a minimum power setting. It will be understood that the opposite may equally be true, in that the first switch setting may be designed for causing the transmission of minimum power to the handpiece 100 and the second switch setting will then cause the transmission of maximum power to the handpiece 100.

The PCBs 290 are thus also designed to provide a circuit having two different switch settings. It will also be appreciated that any number of PCBs 290 may be used in the practice of the present invention so long as the PCBs 290 contain circuits which provide signals to the generator or the like causing the delivery of at least two different levels of power to the handpiece 100 depending upon which portion of the switch button member 270 is contacted by the user. One preferred type of PCB 290 is a dome switch type PCB 290 in which a first dome (not shown) is formed as part of the PCB 290 for generating a first signal (e.g., a maximum power signal) when the first dome is collapsed under an applied force. The dome switch type PCB 290 also includes a second dome (not shown) formed as part of the PCB 290 for generating a second signal (e.g., a minimum power signal) when the second dome is collapsed under an applied force. It will be understood that the switch mechanism 110 of the present invention is not limited to generating signals for controlling the delivery of power to the handpiece 10. The switch mechanism 110 may also be used to generate signals which control other functions of the handpiece 10. For example, the control signals may be used to selectively control console functions, including but not limited to, a stand-by function, a diagnostic function, and turning the console 20 on and off.

The first dome is disposed underneath the first post 276 so that when the user depresses the first raised section 282, the switch button member 270 pivots about the fastener 300 and the first post 276 is directed downwardly through the respective opening formed in the button section 214 until contact is made between the first post 276 and the PCB 290. More specifically, the first post 276 contacts the first dome of the PCB 290 and causes the first dome to collapse. When the first dome collapses, electrical current flows in a first direction through the PCB 290 and generally through the switch mechanism 110. When the user depresses the second raised section 284, the second post 278 contacts and collapses the second dome and causes electrical current to flow in an opposite second direction through the PCB 290 and generally through the switch mechanism 110. It will also be understood that the present invention is not limited to the use of domes but rather any mechanism which serves to close a normally open switch may be used in the practice of the present invention. The collapsing motion of a dome is merely one exemplary way of closing a normally open switch.

As best shown in FIGS. 6 and 7, the switch end cap 200 also includes a second conductive finger element 310 which is disposed about the proximal end of the conductive member 230. In the exemplary embodiment, the second conductive finger element 310 is an annular ring-like member formed of a plurality of fingers 311 radially disposed about the conductive member 230. Each finger 311 of the conductive finger element 310 has a first section 312 which is electrically connected to one of the PCBs 290 and a serially-connected second section 314 which comprises a free end of the finger 311. The free second section 314 makes electrical contact to another conductive member when the handpiece 100 is assembled as will be described in greater detail hereinafter. The second section 314 is preferably bent in several locations so that it assumes a generally zig-zag shape. The first and second conductive finger elements 170, 310 may be formed of any number of suitable conductive materials.

Between the first and second sections 312, 314, each finger 311 connects to a conductive base ring, generally indicated at 316, which provides a conductive path between all of the fingers 311 (FIG. 7). The conductive base ring 316 also is used to properly locate and position the conductive finger element 310 within the switch end cap 200. The annular platform 250 preferably includes a plurality of radially spaced tabs (not shown) which serve to retain the conductive finger element 310 by inserting the conductive base ring 316 underneath the tabs such that the second section 314 of the finger 311 is located between and extends outwardly from adjacent tabs. By anchoring the conductive finger element 310 within the annular platform 250, the second sections 314 of the plurality of fingers 311 may be manipulated and moved in directions generally towards or away from the conductive member 230. The number of fingers 311 may vary depending upon the precise application and in one exemplary embodiment, the conductive finger element 310 includes six (6) fingers 311. The fingers 311 also provide a mechanism for releasably retaining the switch end cap 200 to the flange 160. When the switch end cap 200 is mated with the handpiece body 150, the fingers 311 are flexed inward by engagement with the inner surface of the body 150. This inward flexing of the fingers 311 causes the fingers 311 to apply an outwardly directed biasing force against the flange 160 causing retention between the switch end cap 200 and the body 150. Because the conductive finger element 310 provides, in part, an electrical path for the handpiece 100, it is important that the conductive finger element 310 not touch the conductive member 230. It will be appreciated that the switch end cap 200 preferably includes a number of other spacer members which serve to further isolate the conductive members of the switch end cap 200, namely the element 310 and member 230.

All of the conductor members used in the surgical device 10 (FIG. 1) of the present invention are formed of any number of suitable conductive materials. In one exemplary embodiment, the conductive members are formed of stainless steel, gold plated copper, beryllium copper, titanium nitride, or conductive plastics which serve to reduce the tendency of the members to corrode from harsh cleaning solutions or autoclaving.

The assembly and operation of the handpiece 100 will now be described with reference to FIGS. 1–7. The switch end cap 200 is removably attached to the handpiece body 150 by aligning the stud 156 and the horn 130 with the inside of the conductive member 230. After the stud 156 and the horn 130 are aligned with the bore formed in the conductive member 230, the switch end cap 200 is brought into engagement with flange member 160 causing the stud 156 and a portion of the horn 130 to be disposed inside of the conductive member 230 when the switch end cap 200 is properly fitted about the body 150. However, the stud 156 and the horn 130 do not make contact with the conductive member 230 when switch end cap 200 is attached to the body 150. The proximal end 204 of the switch end cap 200 seats proximate to or against the shoulder 164. As stop 391 formed in the switch end cap 200 engages distal end 152 of the body 150, thereby providing a stop which restricts further movement of the switch end cap 200.

Because the stud 156 and a portion of the horn 130 are disposed inside of the conductive member 230 at a proximal end thereof, the instrument 30 is secured within the switch end cap 200 by securing the instrument 30 to the stud 156. More specifically, the instrument 30 preferably has a threaded bore formed therein at an end opposite the blade tip 36 (FIG. 3). The instrument 30 preferably attaches to the stud 156 by threadingly engaging the threaded bore with the threaded stud 156 resulting in the instrument 30 being secured to the stud 156. The instrument 30 is easily removed for cleaning or replacement thereof by simply twisting the instrument 30 in one direction until the instrument 30 disengages the stud 156. When the instrument 30 is secured to the stud 156, the insulative sheath 34 of the instrument 30 contacts and forms a seal with the seal member 240 so that unwanted foreign matter is prevented from traveling through the opening formed in the distal end 202. Because of the resilient nature of the seal member 240, the seal member 240 conforms to the blade shape and the resilient nature of the insulative sheath 34 further provides an effective seal.

In accordance with another aspect of the present invention, the first and second conductive finger elements 170, 310 provide an electrical pathway between the switch mechanism 110 of the switch end cap 200 and the cable 22, which provides the means for delivering power to the handpiece 100. As best shown in FIG. 7, when the switch end cap 200 is attached to the body 150 and the fingers 171 of the first conductive finger element 170 contact and are biased against an outer surface 231 of the first conductive member 230 of the switch end cap 200. This results because the first conductive member 230 is disposed between the fingers 171 and the horn 130 as the switch end cap 200 is attached. Because of the conductive nature of both the first conductive member 230 and the fingers 171, an electrical pathway is formed between the PCBs 290 and the cable 22. This electrical connection also serves to complete one side of the circuit of the switch mechanism 110 when one of the switch button members 270 is depressed to cause one of the domes to collapse, thereby permitting current to flow through the PCBs 290. Once the user releases either of the first and second raised sections 282, 284 (which the user had previously depressed), the dome expands and the electrical pathway is interrupted, thereby interrupting the flow of current through the switch mechanism 110. This stops the delivery of power to the handpiece 100. It will also be appreciated that the switch mechanism 110 of the present invention may include only a single button member 270.

While, the switch mechanism 110 has been generally discussed as being a normally open switch assembly in which a mechanism (such as one or more domes) is activated to cause the closing of the switch, one of skill in the art will appreciate that the switch mechanism 110 may be a normally closed switch assembly. In this embodiments, depressing one of the sections 282, 284 will cause one of the switches to open and not close as in the other embodiment. Because the dual switch mechanism 110 has current flowing in first and second opposing directions, the opening of one switch will leave current flowing only in a single direction. In this embodiment, the generator or the like will have a sensing mechanism, such as sensing circuit, which is designed to detect the current flowing in the single direction and equate this to the activation of one of the sections 282, 284.

A first electrical pathway is thus specifically defined by the PCBs 290, the fasteners 300, the conductive member 230, the fingers 171 and one or more wires electrically connecting the fingers 171 to the cable 22. In other words, the connection between the fingers 171 and the conductive member 230 serves to electrically bridge the body 150 and the switch mechanism 110 together. Electrical current flows through the cable 22 and then through the one or more wires to the first finger element 170. The current then flows into the switch mechanism 110 by means of the electrical connection between the fingers 171 and the conductive member 230 once the switch mechanism 110 is actuated by manipulation of one of the switch button members 270.

In a similar manner, the fingers 311 of the second conductive finger element 300 contact and are biased against the body 150 of the handpiece 100. Because the body 150 in this embodiment is formed of a conductive member and is electrically connected to one or more wires of the cable 22, the body 150 comprises a conductive member which can be used to complete the circuit of the switch mechanism 110. The fingers 311 are spaced sufficiently away from the conductive member 230 so that the fingers 171 are actually disposed between the fingers 311 and the conductive member 230 when the switch end cap 200 is attached to the body 150.

The resilient nature of the second sections 314 of the fingers 311 permits the fingers 311 to contact the body 150 and flex inwardly or outwardly relative thereto as the switch end cap 200 is attached. Because the first sections 312 of the fingers 311 are electrically connected to the PCBs 290, the contact between the second ends 314 and the body 150 completes the circuit of the switch mechanism 110 and permits current to flow through the body 150 and the second conductive finger element 310 once the switch mechanism 110 is actuated. In other words, a second electrical pathway is formed and is defined by the PCBs 290, the second conductive finger element 310 and the body 150.

The switch mechanism 110 may be though of as including four (4) switches with each having a diode in series. More specifically, first raised section 282 of one switch button member 270 corresponds to a first front switch, the second raised section 284 of the one switch button member 270 corresponding to a first rear switch, the first raised section 282 of the other switch button member 270 corresponding to a second front switch, and the second raised section 284 of the other switch button member 270 corresponding to a second rear switch. It will be understood that each of the aforementioned front and rear switches has a diode in series with one another. Preferably, the first and second front switches have the same diode orientation and the first and second rear switches have the same opposite diode orienation. The polarity of the diode depends upon whether the diode is part of the front or rear switches. When a user depresses one of the first raised sections 282, the corresponding first or second front switch will be actuated due to the associated PCB dome collapsing due to the force applied by one of the first posts 276. This causes current to flow in a first direction through the handpiece 100. When a user depresses one of the second raised sections 284, the corresponding first or second rear switch will be actuated due to the associated PCB dome collapsing due to the force applied by one of the second posts 278. This causes current to flow in an opposite second direction through the handpiece 100. Thus, in this embodiment, there are four domes formed as part of the PCBs 290 with two domes being formed on each PCB 290.

The handpiece 100 may be designed so that the front switches comprise maximum power switches with the front diodes thereof serving to signal the delivery of maximum power to the handpiece 100 for maximum vibration of the instrument 30. In this embodiment, the rear switches comprise minimum power switches with the rear diodes thereof serving to signal the delivery of the minimum power to the handpiece 100 for minimum vibration of the instrument 30. The generator is designed so that upon sensing current in the first direction from the actuation of one of the front switches, the generator is programmed to deliver maximum power to the handpiece 100 and similarly, when the generator senses current in the second direction, the generator delivers minimum power to the handpiece 100. If one of the front switches and one of the rear switches are accidently depressed at the same time, the generator will sense current in both the first and second directions. Upon sensing the opposing currents, the generator is programmed to stop delivering power to the handpiece 100 until the condition is rectified. Preferably, an error or warning message will also appear on the liquid crystal display device 20.

Importantly, the fingers 171 of the first conductive finger element 170 and the fingers 311 of the second conductive finger element 310 do not contact one another during operation of the handpiece 100. If one of the fingers 171 were to contact one of the fingers 311, an electrical short would likely result because the electrical pathways have been crossed. If an electrical short exists in the handpiece 100, the generator will sense current in both the first and second directions, thereby causing the generator to stop delivering power to the handpiece 100 and optionally generate some type of error or warning message.

In another aspect of the present invention, the switch end cap 200 is free to rotate about the handpiece body 150 without disrupting the electrical connection provided between the cable 22 and the switch mechanism 110 housed in the outer shell 201. The one or more ridges 168 formed on the flange member 160 provide annular surfaces for the inner surface 203 of the switch end cap 200 to ride along as the switch end cap 200 is freely rotated about the distal end 154 of the body 150. Because the switch end cap 200 and the body 150 advantageously are electrically connected by the rotatable first and second conductive fingers elements 170, 310, the switch end cap 200 and the body 150 are free to rotate relative to one another without causing an interruption in the flow of current within the handpiece 100. The second sections 174, 314 of the fingers 171, 311, respectively, are sufficiently biased against the corresponding complementary conductive surfaces so that the second sections 174, 314 rotationally slide along these conductive surfaces. Thus, the switch end cap 200 may be rotated about the body 150 to a desired position and continues to remain in electrical communication with the body 150 and the generator regardless of the position of the switch end cap 200. Because most blades 30 are non-symmetrical in nature, the surgeon may prefer to alter the relative position of the switch button members 270 to the instrument 30 which is held in one position within the handpiece 100. The finger elements 170, 310 permit this.

The present invention overcomes the deficiencies of the conventional surgical devices by a means for switch electrical communication without the need for hard wiring. This permits the switch end cap 200 to be easily detached from the body 150 for cleaning and other purposes. For example, the design permits easy inspection of the members providing the electrical communication between the switch end cap 200 and the body 150. Therefore, the integrity of the first and second conductive finger elements 170, 310 may be checked at any time to ensure that they remain in working condition. Also, if the need arises to replace or service either the switch end cap 200 or the handpiece body 150, the two components are quickly and easily separable and replacement or servicing may be done. This permits the surgical operations to continue in an unimpeded manner.

The switch end cap 200 is also ergonomically designed in that the two switch button members 270 are disposed about 180° apart from one another because this provides a preferred orientation where the user (surgeon) may easily contact both switch button members 270 as the handpiece 100 is being grasped by the user. By placing the switch button members 270 in more than one location, the user may easily and quickly manipulate one switch button member 270 closest to the activating finger(s). In other words, it has been found that during a typical manual manipulation of the switch end cap 200, one thumb and one or more fingers are generally positioned 180° apart from another and this complements the positioning of the two switch button members 270. The 180° orientation also has strategic benefits in that if the switch button members 270 were placed at multiple locations, such as three, it would be difficult for the user to grasp the surgical device 10 without possibly contacting and engaging one of the switch button members 270. In the present design, the 180° orientation provides a grasping area in which the user's fingers do not contact the switch button members 270 when the user is holding the device 10. Other design features, e.g., opposing contoured finger sections 212, are designed to also provide the switch end cap 200 with a better feel and permit the user to easily grasp and rotate the switch end cap 200.

The present invention thus provides a surgical handpiece 100 in which the switch mechanism 110 of the switch end cap 200 is electrically connected to the handpiece body 150 in such a manner that permits the switch end cap 200 to be freely rotated about the handpiece body 150 while the electrical connection is maintained.

While the present invention has been described as being a freely rotatable system, it also within the scope of the present invention that the handpiece 100 may be only partially rotatable. In this instance, a number of stoppers or detents (not shown) are incorporated into the structure of the handpiece 100 so that the switch end cap 200 may only be partially rotated with respect to the handpiece body 150. The degree of rotation may thus be selected by the manufacture and the stoppers or detents positioned accordingly. In another embodiment, the detents may be formed so that the switch end cap 200 is rotated incrementally in a ratchet like manner. Once again, these detents may be formed and complementary enageable features are also formed to provide this ratcheting effect. Also, the handpiece 100 may be designed to provide indexable rotation where the rotation of the switch end cap 200 is indexed relative to the instrument 30. For example, the instrument 30 may be designed so that upon being fastened to the horn 130, the instrument 30 always assumes one orientation. For example, the instrument 30 may assume a north-south (vertical) orientation. By using detents and the like, the rotation of the switch end cap 200 may be indexed so that the switch end cap 200 is initially in a predetermined first position and rotation of the switch end cap 200 causes the switch end cap 200 to rotate in predetermined increments, e.g., 90° increments. This permits the most favored positions of the switch end cap 200 to be provided for by the indexed rotation system.

It will also be understood that the present invention broadly discloses a method of providing rotation between the switch end cap 200 and the handpiece body 150 where a predetermined number of conductive pathways are formed by mating electrical conductors. Each pair of mating electrical conductors is designed to convey an independent electrical signal.

Figure 8:
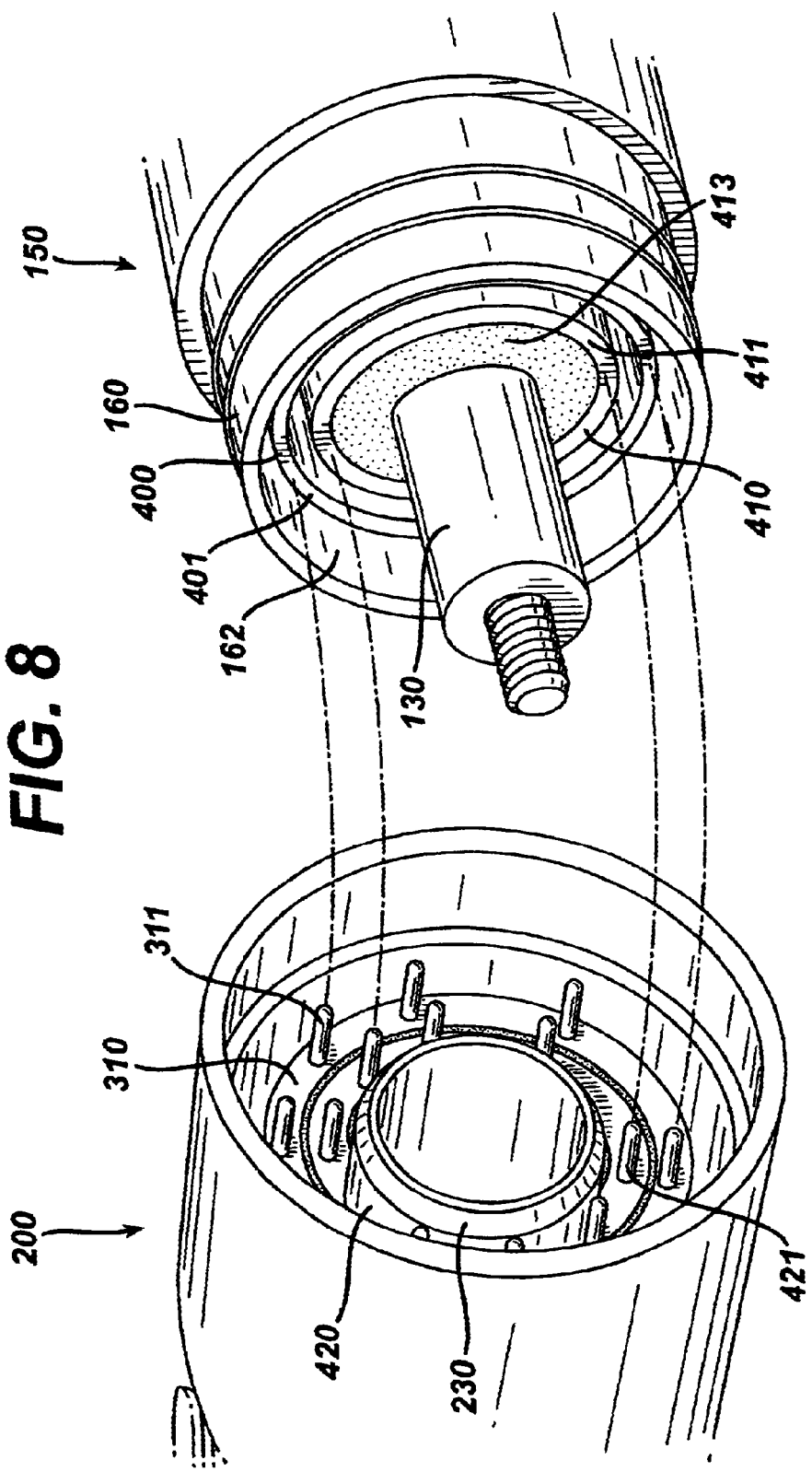
FIG. 8 is a is a fragmentary exploded perspective view of an exemplary handpiece and switch end cap according to a second embodiment.

Turning now to FIG. 8 in which another embodiment of the present invention is illustrated. This embodiment is similar to the first embodiment shown in FIGS. 1–7 in that the handpiece body 150 and the switch mechanism 110 (FIG. 1) disposed within the switch end cap 200 are detachable relative to one another and are electrically connected to one another in such a manner that permits the switch end cap 200 to be freely rotated about the handpiece body 150 while the electrical connection is maintained therebetween. However, the mechanism in this embodiment is different with respect to the second embodiment of FIG. 8. For purpose of illustration, it will be understood that the handpiece body 150 and switch end cap 200 of FIG. 8 are essentially identical to those described in the first embodiment with the differences being noted herein. More specifically, the handpiece body 150 includes a first conductive ring 400 and a second conductive ring 410 which are securely disposed within the handpiece body 150.

In one exemplary embodiment, the first conductive ring 400 comprises a ring member which is disposed between the handpiece body 150 and the horn 130. Preferably the first conductive ring 400 is formed adjacent to the flange member 160 within the cavity 162 and is electrically isolated from other electrical components. The first conductive ring 400 is anchored to and extends upwardly from a non-conductive platform or the like (not shown) which is formed within the handpiece body 150. The first conductive ring 400 is electrically connected to the cable 22 (FIG. 1) by means of one or more electrical wires (not shown) which extend along the length of the body 150 from the electrical adapter 156 (FIG. 3) to the first conductive ring 400.

The second conductive ring 410 of the handpiece body 150 similarly comprises a ring member which is disposed between the handpiece body 150 and the horn 130. The second conductive ring 410 is disposed between the first conductive ring 400 and the horn 130 and therefore the first and second conductive rings 400, 410 are concentric members. The second conductive ring 410 is likewise electrically isolated from the first conductive ring 400 and other electrical components contained within the body 150. Similar to the first conductive ring 400, the second conductive ring 410 preferably is anchored to and extends upwardly from the non-conductive platform. It will be understood that the first and second conductive rings 400, 410 are sufficiently spaced from one another so that they are electrically isolated from each other. This may be accomplished by using one or more spacers 413 disposed between the first and second conductive rings 400, 410 or between the rings 400, 410 and other members within the handpiece body 150. The second conductive ring 410 is also electrically connected to the cable 22 (FIG. 1) by means of one more electrical wires (not shown) which extend along the length of the body 150 from the electrical adapter 156 (FIG. 3) to the second conductive ring 410. The second conductive ring 410 is thus provided to partially define a second electrical pathway from the cable 22 to the switch mechanism 110 (FIG. 4).

It will be appreciated that in this embodiment, the handpiece body 150 is preferably formed of a non-conductive material, such as a plastic material, because both electrical pathways within the handpiece body 150 are defined by the first and second conductive rings 400, 410 (with their respective electric wires) and not the handpiece body 150 itself as in the first embodiment. As will be described in greater detail hereinafter, a first planar contact surface 401 of the first conductive ring 400 and a second planar contact surface 411 of the second conductive ring 410 provide conductive surfaces which engage complementary conductive members of the switch end cap 200 to provide the electrical connection therebetween.

The switch end cap 200 is modified so that the member 230 (FIG. 7) does not serve as a conductive member but rather comprises a member which simply receives the horn 130 and the instrument 30 (FIG. 1). Accordingly, the member 230 is not electrically connected to the PCBs 290 (FIG. 4) and may be formed of a non-conductive material, such as a plastic. In addition to the second conductive element 310 (FIG. 7), the switch end cap 200 of FIG. 8 includes a third conductive element 420. In one exemplary embodiment, the third conductive element 420 comprises an annular ring-like member formed of a plurality of electrical contacts 421 radially disposed about the member 230. The contacts 421 may be in the form of fingers, pins, or the like. The third conductive element 420 is disposed between the second conductive element 310 and the member 230. Similar to the second conductive element 310, the third conductive element 420 is electrically connected to the PCBs 290 (FIG. 4) by means of one or more electric wires (not shown). Thus, the third conductive element 420 and not the member 230 is electrically connected to the PCBs 290 (FIG. 4) to thus complete one side of the circuit of the switch mechanism 110 (FIG. 4) once one of the switch button members 270 (FIG. 4) is depressed to cause one of the domes to collapse, thereby permitting current to flow through the PCBs 290 (FIG. 4).

In accordance with this embodiment of the present invention, the second and third conductive elements 310, 420 and the first and second conductive rings 400, 410 provide first and second electrical pathways between the switch mechanism 110 (FIG. 1) of the switch end cap 200 and the cable 22 (FIG. 1), which provides the means for delivering power to the handpiece 100 (shown entirely in FIG. 1). More specifically, when the switch end cap 200 mates with the handpiece 100, the second conductive element 310 engages the first planar contact surface 401 of the first conductive ring 400 to establish the first electrical pathway. Because the second conductive element 310 comprises an annular member having radially spaced contacts 311, the rotation of the switch end cap 200 causes the contacts 311 to ride along the first planar contact surface 401. Contacts 311 may be in the form of conductive fingers, pins, or the like. As the switch end cap 200 is rotated and the contacts 311 ride along the surface 401, the first electrical pathway is maintained.

Similarly, the contacts 421 of the third conductive finger element 420 engage the second planar contact surface 411 of the second conductive ring 410 to establish the second electrical pathway. Because both the third conductive finger element 420 and the second conductive ring 410 comprise annular members, the switch end cap 200 may be freely rotated without disruption of the electrical connection between the switch mechanism 110 (FIG. 4) and the handpiece 100. In this embodiment, the contacts 311, 421 are generally disposed longitudinal to the first and second conductive rings 400, 410.

The rotatable connection between the contacts 311, 421 and the first and second rings 400, 410 serves to electrically bridge the body 150 and the switch mechanism 110 (FIG. 4) together. Electrical current flows through the cable 22 (FIG. 1) and then through the electrical wires to the first and second conductive rings 400, 410. The current then flows through the fingers 311, 421 to the switch mechanism 110 (FIG. 4) once the switch mechanism 100 (FIG. 4) is actuated by manipulation on one of the switch button members 270 (FIG. 4). Once the user depresses one of the first and second raised sections 282, 284 (FIG. 4), one of the domes is collapsed, thereby permitting current to flow through the PCBs 290 (FIG. 4). Once the user releases either of the first and second raised sections 282, 284 (FIG. 4), the dome expands and the electrical pathway is interrupted, thereby interrupting the flow of current through the switch mechanism 110 (FIG. 4). This stops of the delivery of power to the handpiece 100.

The operation of the switch mechanism 110 (FIG. 4) in this embodiment is essentially the same as the operation in the first embodiment of FIGS. 1–7 and therefore will not be described in greater detail. It will also be appreciated that depending upon the number of switches included in the switch mechanism 110 (FIG. 4), the number of complementary and mating contact-ring members will vary. For example, while FIG. 8 shows two sets of contact-ring assemblies, it will be appreciated that additional contact-ring assemblies can be added to the switch end cap 200 and the body 150, respectively. It will also be appreciated that the placement of the first and second conductive elements 310 and 420 and the first and second conductive rings 400, 410 may be reversed. In other words, the first and second conductive rings 400, 410 may be provided in the switch end cap 200 with each being electrically connected to the PCBs 290 (FIG. 4) by means such as an electric wire. The first and second conductive elements 310, 420 are disposed within the body 150 and preferably within the flange 160 thereof. The first and second conductive elements 310, 420 are electrically connected to the cable 22 (FIG. 1) by means such as electrical wires between each element 310, 420 and the cable 22 (FIG. 1). The operation of the device is the same because a rotatable electrical connection is provided between the handpiece 100 and the switch mechanism 110 (FIG. 4) disposed within the switch end cap 200.

It will be appreciated that the second and third conductive elements 310, 420 and the first and second conductive rings 400, 410 are formed of a conductive material, such as stainless steel or gold plated copper. It will also be appreciated that instead of containing a plurality of conductive contacts, each of the second and third conductive elements 310, 420 may comprise a single conductive finger. The inclusion of an array of commonly connected conductive fingers (as shown in FIGS. 1–8) provides increased contact robustness because if one of the fingers becomes inoperative, there are a number of other contacts which serve to provide the electrical connection. Furthermore, the second and third conductive elements 310, 420 are spaced sufficiently from each other so that the individual contacts do not contact one another during operational coupling of the switch end cap 200 to the handpiece body 150. If the first and second conductive elements 310, 420 were to contact one another, a short circuit condition would likely result.

Accordingly, this embodiment, as with the first embodiment, provides a surgical device in which the switch mechanism 110 (FIG. 4) of the switch end cap 200 is electrically connected to the handpiece body 150 in such a manner that permits the switch end cap 200 to be freely rotated about the handpiece body 150 while the electrical connection is maintained. Advantageously, the electrical communication of the switch does not require hard wiring. This permits the switch end cap 200 to be detachable from the body 150 and also permits rotation of the switch end cap 200 so that the user easily adjust its position during an operation.

Figure 9:
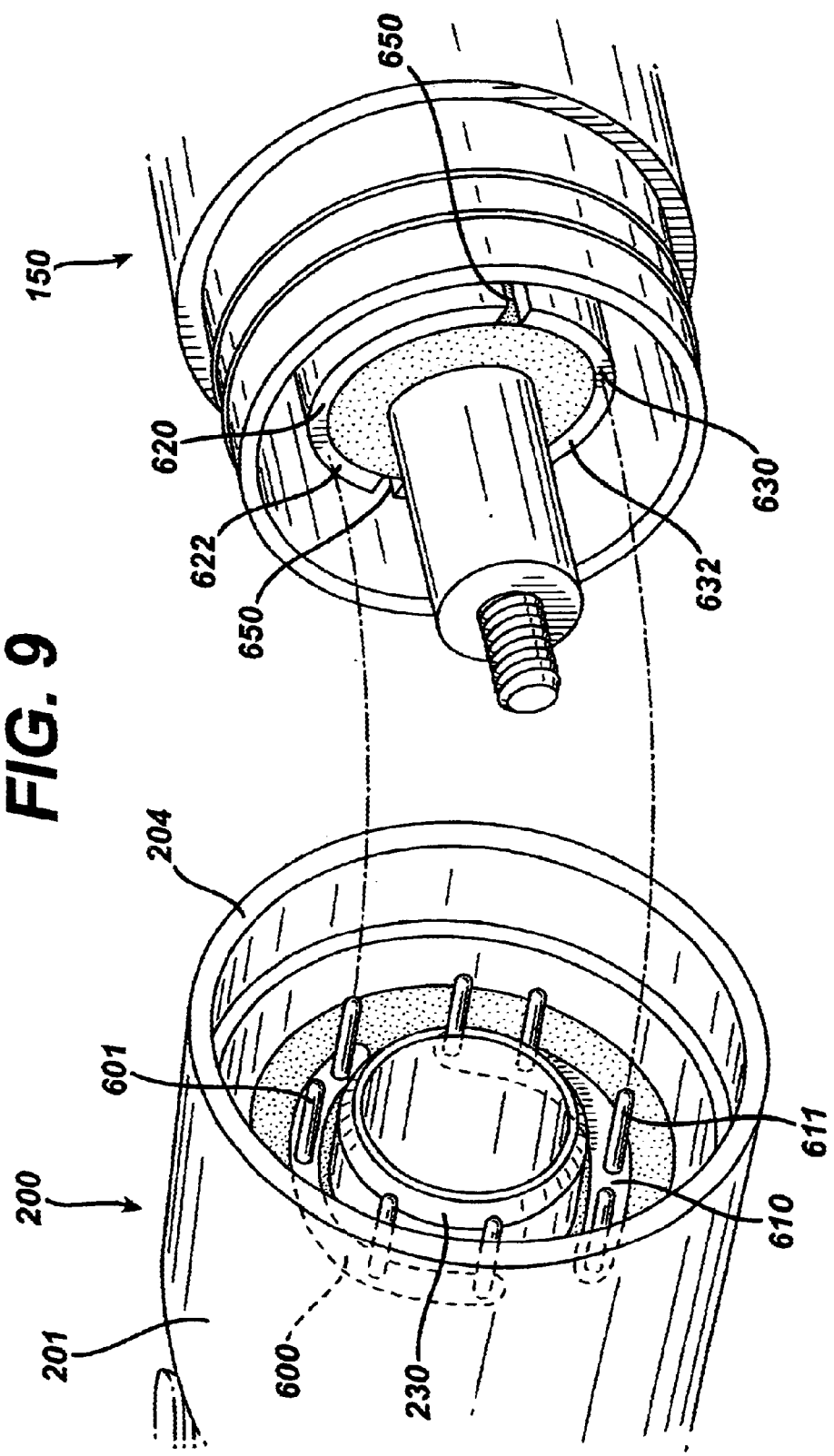
FIG. 9 is a fragmentary exploded perspective view of an exemplary handpiece and switch end cap according to a third embodiment.

Turning now to FIG. 9 in which another embodiment of the present invention is shown. In this embodiment, the switch end cap 200 has a first conductive element 600 and a second conductive element 610. As with the embodiment of FIG. 8, in this embodiment, the member 230 does not serve as a conductive member for electrically connecting the PCBs 290 (FIG. 4) to the cable 22 (FIG. 1). Instead, the member 230 comprises a member which receives the horn 130 and the instrument 30 (FIG. 1). It will be appreciated that the member 230 may therefore be formed of a conductive material or a non-conductive material.

In the exemplary embodiment, the first conductive element 600 is annular in shape; however, it is not in the shape of an annular ring as in the other embodiments, but rather preferably comprises a semi-circular member. The first conductive element 600 is disposed between the member 230 and the outer shell 201 of the switch end cap 200. The first conductive element 600 includes one or more contacts 601 which extend outwardly toward the proximal end 204 of the switch end cap 200. The contacts 601 may be in the form of conductive fingers, pins, or the like. The first conductive element 600 is electrically connected to the PCBs 290 (FIG. 4) by means of one or more electrical wires or the like. Similarly, the second conductive element 610 preferably comprises a semi-circular member which is also disposed between the member 230 and the outer shell 201 opposite the first conductive element 600. The second conductive element 610 includes one or more contacts 611 which extend toward the proximal end 204. The contacts 611 may be in the form of conductive fingers, pins, or the like. The second conductive element 610 is electrically connected to the PCBs 290 (FIG. 4) by means of one or more electrical wires of the like. Preferably, a common radius exists between fingers 601 and the member 230 and the contacts 611 and the member 230.

Figure 10:
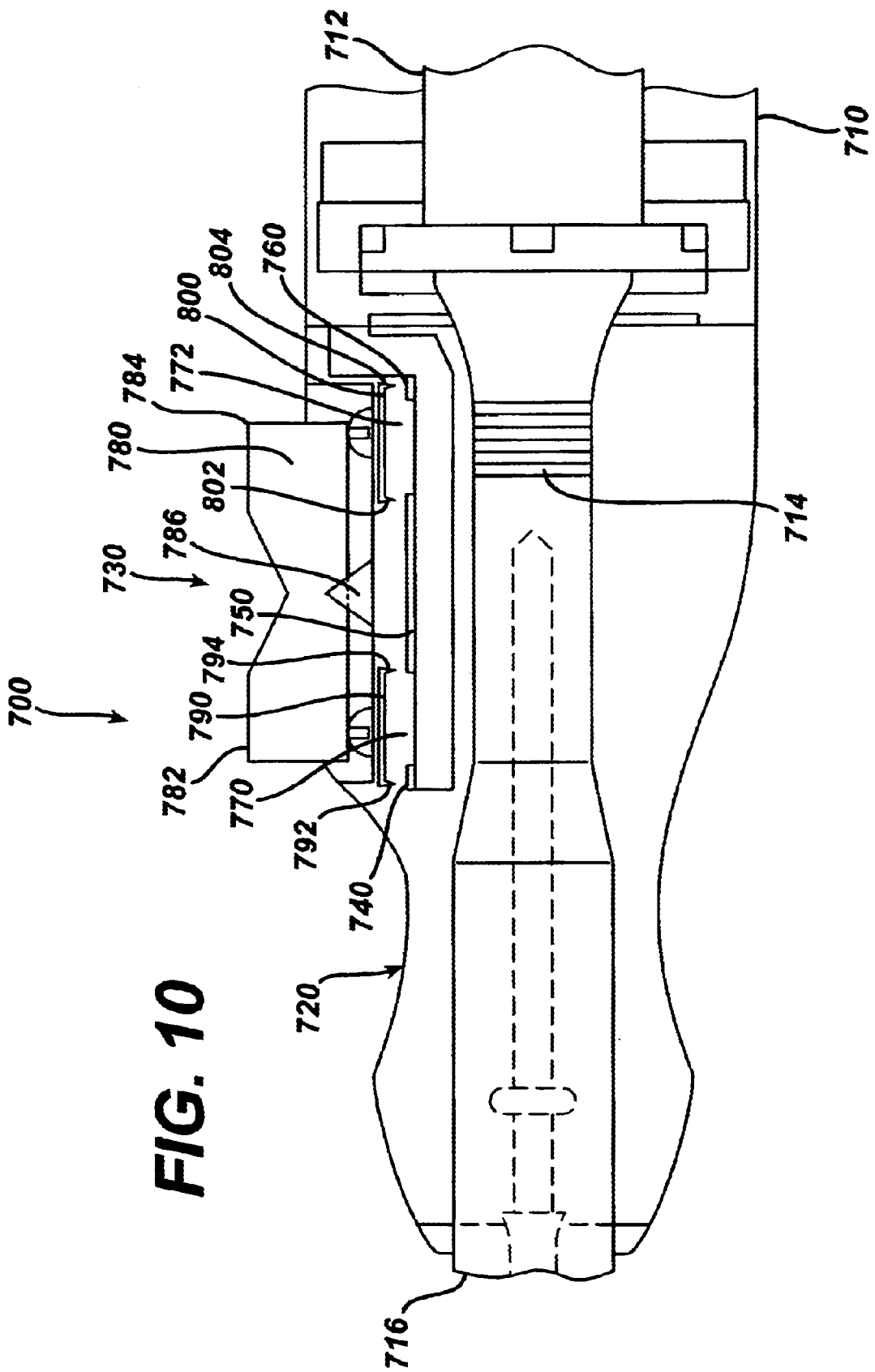
FIG. 10 is a longitudinal cross-sectional view of a rotatable surgical device according to another embodiment of the present invention.

In this embodiment, the handpiece body 150 has a first conductive member 620 and a second conductive member 630. As shown in FIG. 10, each of the first and second conductive members 620, 630 preferably has a semi-circular shape so as to complement the first and second conductive elements 600, 610. More specifically, the first conductive member 620 is disposed about the horn 130 and the second conductive member 630 is also disposed about the horn 130 opposite the first conductive member 620. A gap 650 is formed between each end of the first conductive member 620 and each end of the second conductive member 630. It will be appreciated that if the first and second conductive members 620, 630 were joined together, a continuous annular conductive ring would be formed. The first and second conductive members 620, 630 are formed in the body 150 (preferably between the flange 160 thereof) so that each is electrically isolated from other conductive members. For example, one or more insulating spacers (not shown) may be used to accomplish this.

The first conductive member 620 is electrically connected to the cable 22 (FIG. 1) by means of one or more electric wires (not shown) and the second conductive member 630 is likewise electrically connected to the cable 22 (FIG. 1) by means of one or more electric wires (not shown). Thus, this embodiment has the electrical features of two concentric conductive rings in a single segmented ring structure. This advantageously requires the body 150 to house one "ring width" rather than two and therefore provides an attractive alternative design when the body 150 has limited space for receiving conductive ring members.

The switch end cap 200 of this embodiment mates with the body 150 in a similar manner as that previously described with reference to the embodiment of FIG. 8. For purpose of illustration only, the first conductive element 600 will be described as mating with the first conductive member 620 and the second conductive element 610 will be described as mating with the second conductive member 630. The first conductive member 620 has a first planar contact surface 622 and the second conductive member 630 has a second planar contact surface 632. An electrical connection is formed between the switch mechanism 110 (FIG. 4) and the handpiece body 150 by mating the switch end cap 200 with the body 150 such that the first conductive element 600 engages the first planar contact surface 622 and the second conductive element 610 engages the second planar contact surface 632 when the switch end cap 200 is securely yet rotatably coupled to the body 150.

The contacts 601, 611 are free to rotate in an electrically conductive manner about a majority of the annular rotation range defined by the first and second conductive members 620, 630. More specifically, the only location where one of the contacts 601, 611 is not in electrical contact with one of the members 620, 630 is in one of the gaps 650. As the user rotates the switch end cap 200 relative to the body 150, the contacts 601, 611 travel about the respective first and second planar contact surfaces 622, 632 and then cross over one of the gaps 650 to the other of the first and second planar contact surfaces 622, 632.

The operation of the switch mechanism 110 (FIG. 4) in this embodiment is the same as or similar to the operation described with reference to earlier embodiments. While, the first and second conductive elements 600, 610 have each been described as containing a number of contacts 601, 611, respectively, it will be understood that a single conductive contact may be provided for each element. Because of the electrical pathways provided between the elements 600, 610 and members 620, 630, the switch mechanism 110 (FIG. 4) is electrically connected to the cable 22 (FIG. 1) in such a manner that the switch end cap 200 is freely rotatably and the switch end cap 200 is not hard wired to the body 150.

Turning now to FIG. 10 in which yet another embodiment of the present invention is illustrated. In this embodiment, a surgical device is provided and generally indicated at 700. The surgical device 700 includes a handpiece 710, partially shown, and a switch end cap, generally indicated at 720 with a switch mechanism 730 being formed therein. As with the other embodiments, the surgical device 700 is preferably an ultrasonic surgical device with the handpiece 710 housing a pizoelectric transducer, generally indicated at 712, for converting electric energy to mechanical energy that results in longitudinal vibrational motion of the ends of the transducer. A horn 714 is coupled to the transducer 710 with the surgical blade, generally indicated at 716, being attached to the horn 714. Thus, the blade 716 vibrates in the longitudinal direction at the ultrasonic frequency rate of the transducer 710.

According to this embodiment, a first conductive band 740 is provided as part of the handpiece 710. The first conductive band 740 preferably comprises a continuous annular band which extends around an internal member of the handpiece 710, such as the horn 714. The handpiece 710 also includes a second conductive band 750 which preferably also comprises a continuous annular band extending around the horn 714. A third conductive band 760 is disposed around the horn 714 with the second conductive band 750 being disposed between the first and third conductive bands 740, 760. The third conductive band 760 also preferably comprises a continuous annular band. Each of the bands 740, 750, 760 has a width and is arranged such that a first gap 770 is formed between the first and second bands 740, 750 and a second gap 772 is formed between the second and third bands 750, 760. Each of the bands 740, 750, 760 is electrically connected to an electrical adapter and cable assembly (not shown) of the handpiece 710 which provides power to the handpiece 100. Preferably, one or more electric wires (not shown) are used to electrically connect each of the bands 740, 750, 760 the electrical adapter and cable assembly.

Unlike the switch mechanism 110 (FIG. 4) of the other embodiments, the switch mechanism 730 of this embodiment comprises a simple mechanical mechanism for providing an electric current between the switch mechanism 730 and the handpiece 710 where the switch end cap 720 is freely rotatable during operation without disrupting the electrical connection therebetween. The switch mechanism 730 is generally formed of one or more switch button members 780. In the case that more than one switch button members 780 are used, the switch button members 780 are spaced apart from one another, e.g., 180° spacing when two switch button members 780. Each switch button member 780 has a first depressable portion 782 and a second depressable portion 784. The switch button member 780 may be in the form of a rocker type switch having a center pivot portion 786 to permit the switch button member 780 to pivot thereabout depending upon which one of the first and second depressable portions 782, 784 is depressed.

The switch button member 780 has a first conductive member 790 having a first protrusion 792 formed at one end and a second protrusion 794 formed at the opposite end. The switch button member 780 also includes a second conductive member 800 having a first protrusion 802 formed at one end and a second protrusion 804 formed at the opposite end. In one exemplary embodiment, the first and second protrusions 792, 802, 794, 804, respectively, each comprises a tooth extending outwardly from the remaining portion of the first and second conductive members 790, 800.

This embodiment illustrates the use of the first and second conductive member 790, 800 as switches. The first conductive member 790 is attached to the switch button member 780 at the end which includes the first depressable portion 782 and the second conductive member 800 is attached to the switch button member 800 at the opposite end which includes the second depressable portion 784. Preferably, the first and second conductive members 790, 800 have a width similar to the width of the switch button member 780 so that the members 790, 800 lie beneath the switch button member 780.

In a disengaged position of the switch button member 780, the first protrusion 792 is positioned above the first conductive band 740 and the second protrusion 794 is positioned above the second conductive band 750. The second protrusion 804 of the second conductive member 800 is also positioned above the second conductive band 750 at an opposite thereof relative to the position of the second protrusion 794. The first protrusion 802 is positioned above the third conductive band 760. It will be appreciated that the bands 740, 750, 760 may have different widths; however, the second conductive band 750 is preferably wider than the first and third conductive bands 740, 760 because both the first and second conductive members 790, 800 engage the second conductive band 750.

In operation, the user will depress one of the first and second depressable portions 782, 784 of the switch button member 780 to cause current to flow from a generator (not shown) to the handpiece 710 for causing vibration of the blade 716. For example, if the user depresses the first depressable portion 782, the first protrusion 792 engages the first conductive band 740 and the second protrusion 794 engages the second conductive band 750. An electrical connection is thus provided by bridging the first and second conductive bands 740, 750 together using the first conductive member 790. As long as the first depressable portion 782 remains depressed, current can flow between the first and second conductive bands 740, 750 to complete one electrical path resulting in power being delivered to the handpiece 710. As soon as the first depressable portion 782 is released, the bridge between the first and second conductive bands 740, 750 is eliminated and power is no longer delivered to the handpiece 710.

Similarly, if the user depresses the second depressable portion 784, the first protrusion 802 engages the third conductive member 760 and the second protrusion 804 engages the second conductive member 750. An electrical connection is thus provided by bridging the second and third conductive bands 750, 760 together using the second conductive member 800. As long as the second depressable portion 784 remains depressed, current can flow between the second and third conductive bands 750, 760 to complete one electrical path resulting in power being delivered to the handpiece 710. As soon as the second depressable portion 784 is released, the bridge between the second and third conductive bands 750, 760 is eliminated and power is no longer delivered to the handpiece 710.

In this embodiment, the first and second conductive members 790, 800 thus act as switches by providing a bridge electrically connecting two respective conductive members which are electrically connected to a power supply. Thus, once the bridge is in place, the electrical path is completed and power is delivered to the handpiece 710. Depending upon the desired configuration of the switch mechanism 730, the first depressable portion 782 may be used to provide a first level of power to the handpiece 710 and the second depressable portion 784 may be used to provide a second level of power to the handpiece 710. It will also be understood that the additional conductive bands and complementary conductive members may be provided in the device 700 for providing additional switches.

It will be appreciated that the switch end cap 720 is rotatable relative to the handpiece 710 such that the electrical connection therebetween is not interrupted during the rotation of the switch end cap 720 when one of the first and second depressable portions 782, 784 is actuated. This results because the respective first and second protrusions remain engaged with the respective conductive bands by simply sliding across the surface of the conductive bands as the switch end cap 720 is rotated. Because the conductive bands are annular in nature and extend around the complete circumference of the handpiece 710, the electrical connection is maintained as the switch end cap 720 is rotated to any position about the handpiece 710.

This embodiment provides a much simpler switch mechanism than the other embodiments; however, the switch end cap 720 may still be rotated without disrupting the electrical connection and no hard wires are needed between the handpiece 710 and the switch end cap 720.

Figure 11:
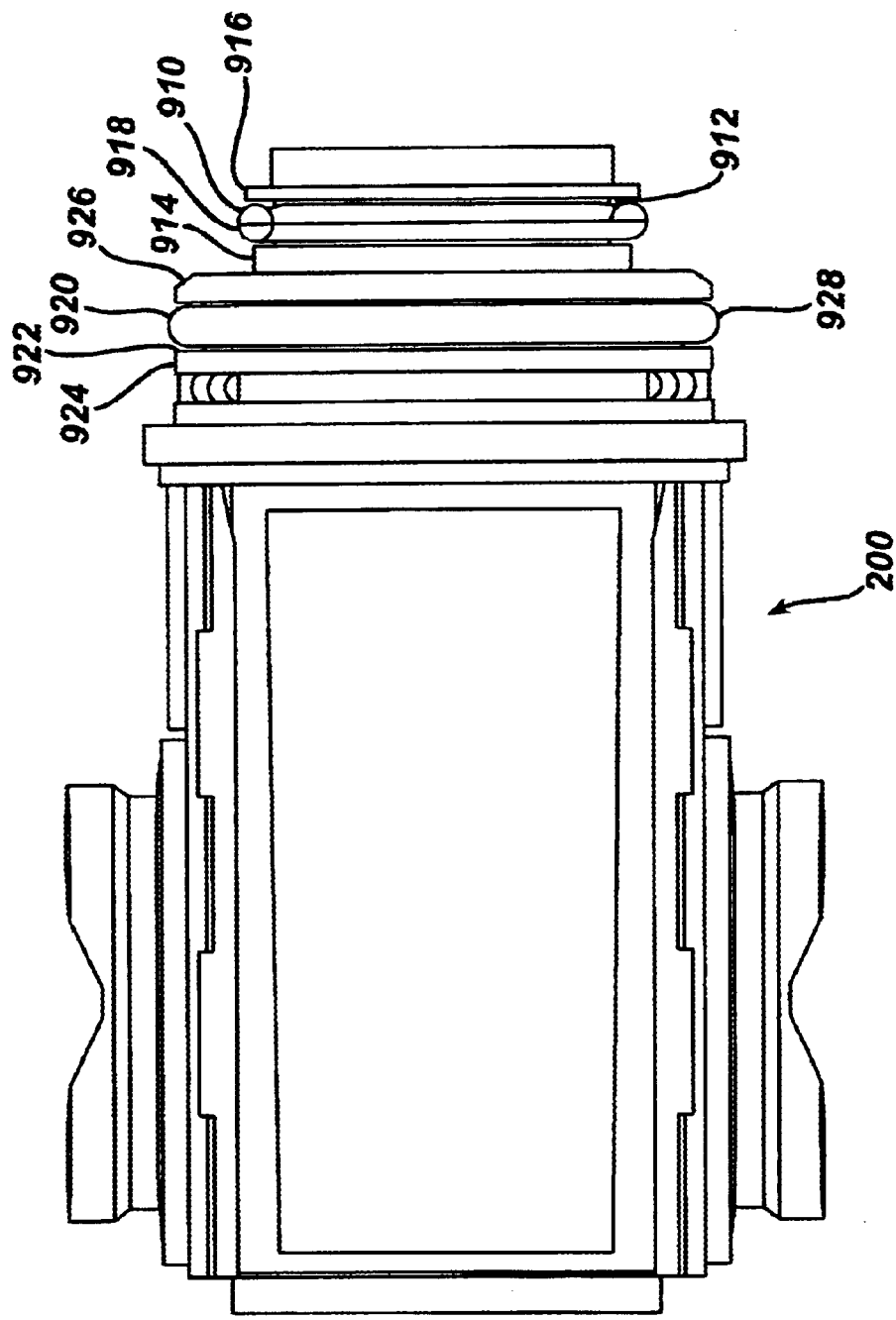
FIG. 11 is a side view of a switch end cap according to a fourth embodiment with the outer shell being removed therefrom.
Figure 12:
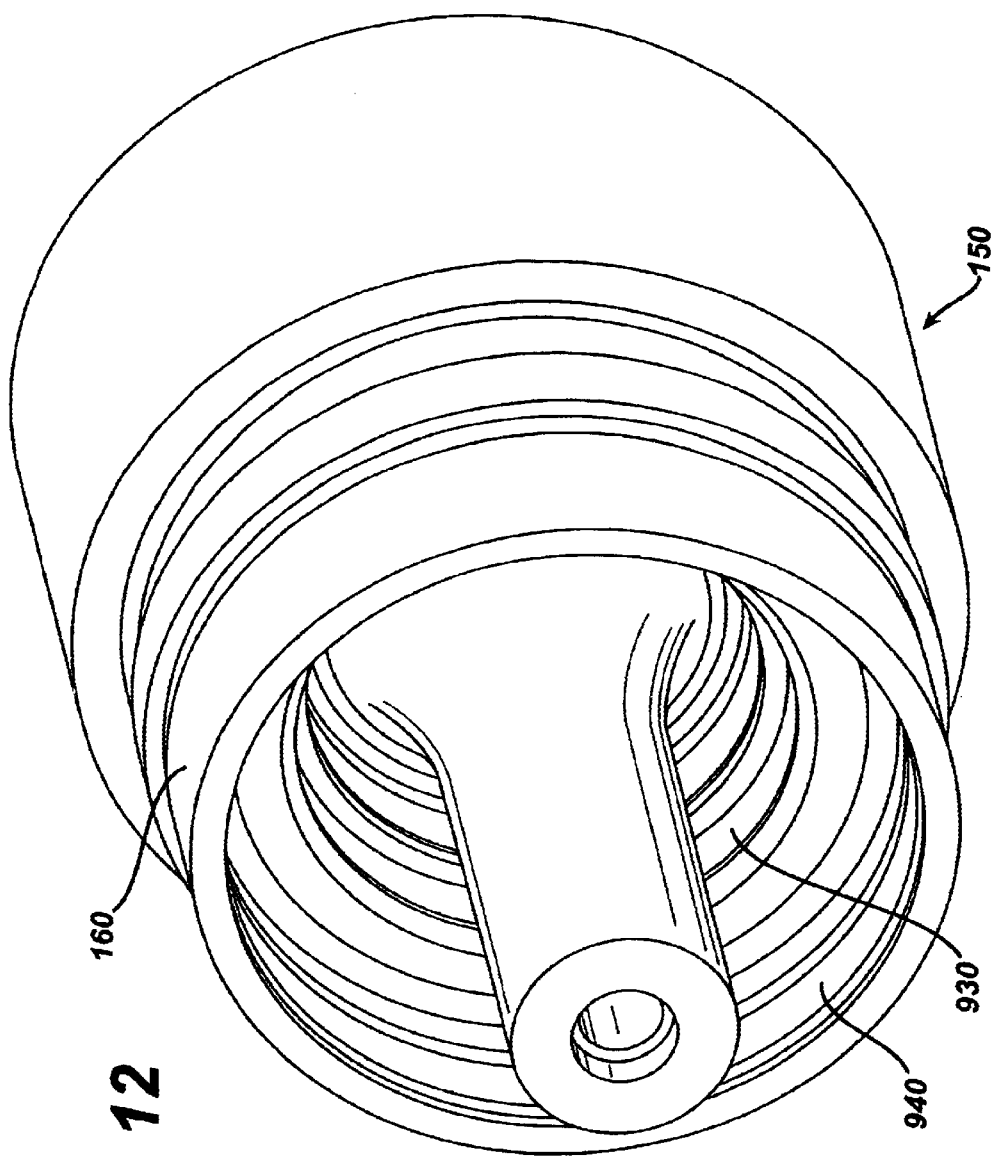
FIG. 12 is a fragmentary perspective view of an exemplary handpiece according to a fourth embodiment.
Figure 13:
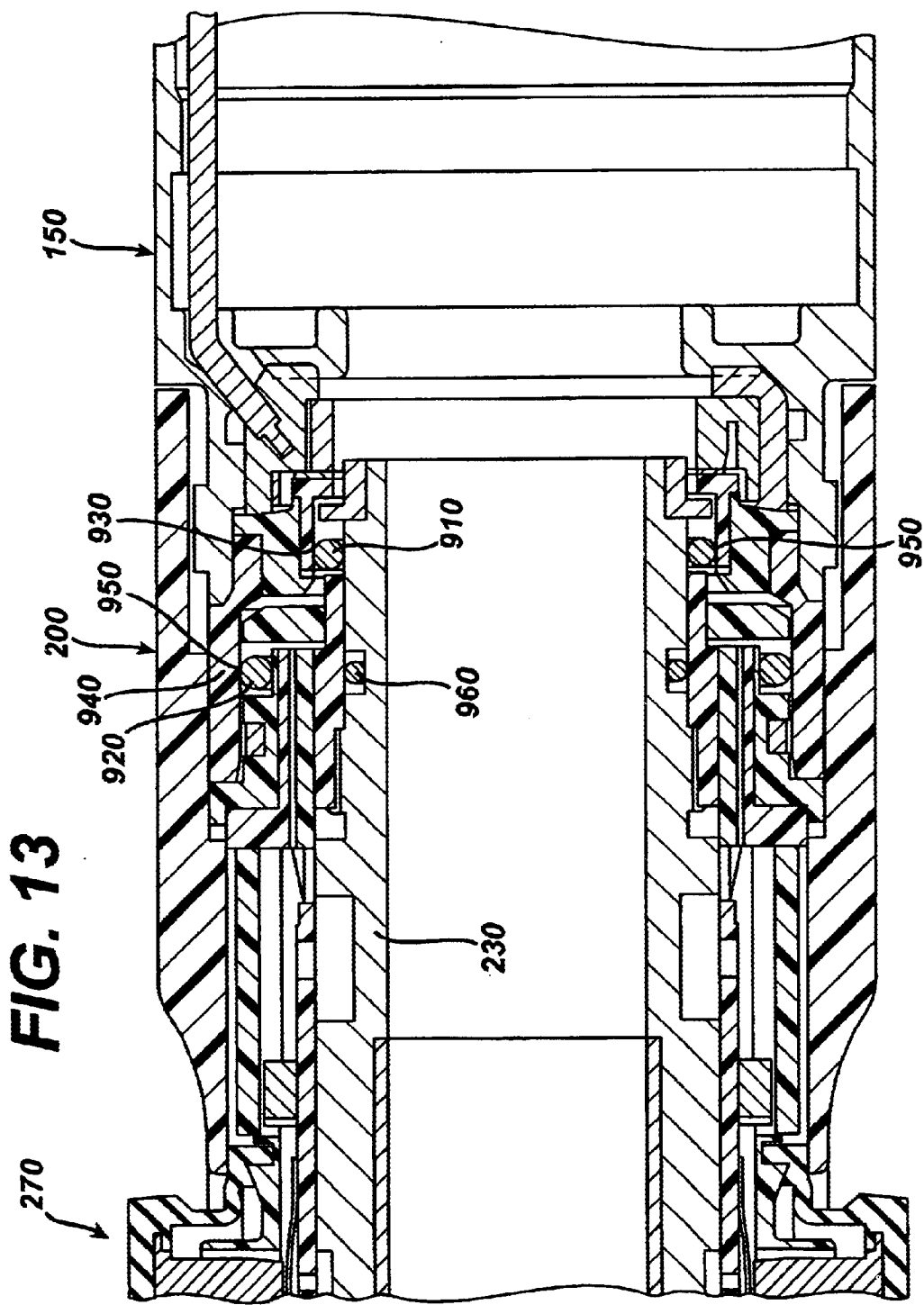
FIG. 13 is a fragmentary enlarged cross-sectional view of the electrical connection between the switch end cap of the embodiment of FIG. 11 and the handpiece body of FIG. 12.

Referring now to FIGS. 11–13 in which another embodiment of the present invention is illustrated. This embodiment is similar to the embodiments illustrated in FIGS. 1–9 in that the switch end cap 200 mates with the handpiece body 150 to form an electrical connection therebetween. In this embodiment, the first end cap 200 has a first conductive member 910 and a second conductive member 920 which mate respectively with a third conductive member 930 and a fourth conductive member 940 disposed within the handpiece body 150. For purpose of simplicity, FIG. 11 illustrates the switch end cap 200 without the outer shell 201 so that the first and second conductive members 910, 920 may be better viewed. The first conductive member 910 is retained within a first gap or channel 912 formed in the switch end cap 200. The first channel 912 is defined by opposing first and second members 914, 916 with the first channel 912 being defined therebetween. It will be understood that the first and second members 914, 916 preferably comprise insulative members which isolate the first conductive member 910. In the exemplary embodiment shown, each of the first conductive member 910 and the first and second members 914, 916 has an annular shape. Preferably, the first conductive member 910 is in the form of an O-ring which is retained within the channel 912 between the members 914, 916. When the first conductive member 910 is seated within the channel 912, a portion 918 generally protrudes above the outer surfaces of the members 914, 916. This portion 918 serves as the conductive contact surface for the first conductive member 910.

Similarly, the second conductive member 920 is retained within a second gap or channel 922 formed in the switch end cap 200. The second channel 914 is defined by opposing third and fourth members 924, 926 with the second channel 922 being defined therebetween. The third and fourth member 924, 926 preferably comprise insulative members which isolate the second conductive member 920. Like the first conductive member 910, the second conductive member 920 is preferably an O-ring which is retained within the second channel 922. When the second conductive member 920 is seated within the second channel 922, a portion 928 generally protrudes above the outer surface of the members 924, 926 and is designed to provide a conductive contact surface.

In this embodiment, as in the embodiment of FIG. 8, the member 230 does not serve as a conductive member but rather comprises a member which simply receives the horn 130 and instrument 30. The first and second conductive members 910, 920 are each electrically connected to the PCBs 290 (FIG. 4) to form one side of the circuit of the switch mechanism 110. The electrical connection between each of the first and second conductive members 910, 920 and the PCBs 290 (FIG. 4) may be formed using any number of techniques including wiring the first and second conductive members 910, 920 to the PCBs 290.

Referring now to FIG. 12 in which the handpiece body 150 is shown in greater detail. In this embodiment, the handpiece body 150 is similar to the handpiece body 150 shown and described with reference to FIG. 8 in that the handpiece body 150 includes complementary conductive members which mate with the first and second conductive members 910, 920 of the switch end cap 200 to provide the electrical connection between the switch end cap 200 and the handpiece body 150. More specifically, the handpiece body 150 includes third and fourth conductive members 930, 940 which mate respectively with the first and second conductive members 910, 920. In one exemplary embodiment, each of the third and fourth conductive members 930, 940 comprises a conductive strip which is disposed within the flange 160 section of the handpiece body 150. Because of the general annular nature of the handpiece body 150, the third and fourth conductive members 930, 940 likewise have an annular shape. The third and fourth conductive members 930, 940 are disposed within the handpiece body 150 so that each one is electrically isolated from the other. In other words, one or more spacers formed of an insulative material are disposed between the third and fourth conductive members 930, 940. Each of the third and fourth conductive members 930, 940 is electrically connected to the cable 22 (FIG. 1).

As best shown in FIG. 13, in another aspect of this embodiment, the third and fourth conductive members 930, 940 each include a slight recessed section, generally indicated at 950, which serve as a retaining feature for capturing the respective first or second conductive member 910, 920. Because the first and second conductive members 910, 920 preferably comprise conductive coil springs in the form of O-rings, the members 910, 920 store and release energy depending upon whether the rings are compressed or not. When the switch end cap 200 mates with the handpiece body 150, the first conductive member 910 seats within the recessed section 950 formed in the third conductive member 930 and the second conductive member 920 seats within the recessed section 950 formed in the fourth conductive member 940. The first and second conductive members 910, 920 thus serve as detents which are received within the sections 950 because of the resilient nature thereof. In other words, when the switch end cap 200 is initially mated with the handpiece body 150, the first and second conductive members 910, 920 are compressed by the inner surface of the flange 160 and upon meeting the sections 950, the members 910, 920 flex outwardly into the sections 950. The sections 950 thus serve to locate the first and second members 910, 920 against the third and fourth members 930, 940 so that electrical connection results therebetween.

In this embodiment, a seal 960 is also preferably provided to ensure a secure fit between the switch end cap 200 and the handpiece body 150 when the two mate together. This seal 960 is preferably formed of a resilient material such as an elastomer. The switch end cap 200 and the handpiece body 150 are rotatable relative to one another as during rotation, the first and second conductive members 910, 920 simply travel within the recessed sections 950 and continuously remain in electrical contact with the third and fourth conductive members 930, 940, respectively. In the illustrated embodiment, the diameter of the first conductive member 910 is less than a diameter of the second conductive member 920 to complement the shape of the handpiece body 150. As with the other embodiments, when an electrical connection is formed between the switch end cap 200 and the handpiece body 150, the power is delivered from the generator (not shown) through the cable 22 and then along two electrical pathways. The first electrical pathway is defined by the first and third conductive members 910, 930 and the second electrical pathway is defined by the second and fourth conductive members 920, 940. It will be understood that there may only be a single electrical pathway or there may be more than two electrical pathways with each pathway being defined by one pair of complementary conductive members.

In another aspect of the present invention, the present invention provides a mechanism for ensuring that the effect of debris and other foreign conductive material on the mating conductive contacts be mitigated. Surface oxidation or debris or other foreign matter that could interfere with conduction between the contacts. By removing these materials, robust conductive contact may be restored. In the present invention, there are at least two forms of frictional contact/scraping action that re-establishes robust contact between intended surfaces. The first, is that the insertion of the switch end cap 200 into the main handpiece body 150 results in contact flexure and frictional rubbing as the contacts engage and become fully seated against each other. Second, rotational adjustment of the switch end cap 200, while initially orientating the switches to align with the desired blade symmetry or reorientation during use causes a wiping action between the contacts. This wiping action wipes the contact surfaces clean and also friction rubbing of the contacts abrades away oxides.

While the invention has been particularly shown and described with reference to the preferred embodiments thereof, it will be understood by those skilled in the art that various changes in form and detail may be made therein without departing from the spirit and scope of the invention.

What is claimed is:

1. A surgical instrument handpiece comprising:
   a handpiece body having distal and proximal ends, the proximal end receiving an electrical cable for providing power to the handpiece, the handpiece body including a first conductive member;
   a switch end cap connected to the handpiece body, the switch end cap including a switch mechanism for selectively controlling delivery of power to the handpiece, the switch end cap having a second conductive member which mates with the first conductive member to provide an electrical connection between the handpiece body and the switch end cap, the switch end cap being rotatable about the handpiece body while the electrical connection is maintained between the handpiece body and the switch end cap; and
   an instrument detachably connected to the handpiece body.

2. The surgical instrument handpiece of claim 1, wherein the instrument is ultrasonically vibrated for performing a surgical operation.

3. The surgical instrument handpiece of claim 1, wherein the handpiece body includes a horn member disposed therein and extending along a longitudinal axis thereof, the instrument being detachably connected to one end of the horn member.

4. The surgical instrument handpiece of claim 1, wherein the first conductive member comprises a first conductive ring element disposed within the handpiece body so that the first conductive ring element intimately contacts the second conductive member to provide the electrical connection.

5. The surgical instrument handpiece of claim 4, wherein the first conductive ring element includes a plurality of conductive fingers connected in an annular ring, the fingers contacting and seating against a conductive bore member disposed within the switch end cap, the instrument extending through an opening formed through the conductive bore member so that a portion thereof extends beyond the switch end cap.

6. The surgical instrument handpiece of claim 4, wherein the handpiece body is formed of a conductive material so that the handpiece body itself acts as a conductive body contact.

7. The surgical instrument handpiece of claim 6, wherein the first conductive ring element includes a plurality of conductive fingers connected in an annular ring, the fingers being radially spaced within a cavity formed at the distal end of the handpiece body, the plurality of fingers being electrically isolated from the conductive body by a spacer member disposed therebetween.

8. The surgical instrument handpiece of claim 6, wherein the conductive body contact is electrically connected to the electrical cable.

9. The surgical instrument handpiece of claim 4, wherein the first conductive ring element is electrically connected to the electrical cable by at least one wire.

10. The surgical instrument handpiece of claim 4, wherein the handpiece body includes a flange member formed at the distal end thereof, a portion of an outer shell of the switch end cap being detachably connected about the flange member.

11. The surgical instrument handpiece of claim 1, wherein the switch end cap includes an outer shell having a bore extending therethrough from the distal end to the proximal end.

12. The surgical instrument handpiece of claim 11, wherein the switch mechanism includes one or more switch button members operatively attached to the outer shell, each of the one or more switch button members having a first switch setting and a second switch setting.

13. The surgical instrument handpiece of claim 12, wherein the first switch setting is a maximum power setting and the second switch setting is a minimum power setting.

14. The surgical instrument handpiece of claim 12, wherein activation of one of the first and second switch settings controls turning on or off certain preselected console functions.

15. The surgical instrument handpiece of claim 11, wherein the one or more switch button members each are formed with an inactive center region for resting of a finger without inadvertently activating the handpiece.

16. The surgical instrument handpiece of claim 1, wherein the switch mechanism includes at least one printed circuit board disposed within the switch end cap, the printed circuit board being electrically connected to the first conductive member so that actuation of the switch mechanism causes current to flow through the printed circuit board and the instrument is vibrated.

17. The surgical instrument handpiece of claim 1, wherein the switch mechanism comprises:
a pair of printed circuit boards disposed about a conductive bore member extending through the switch end cap,
a pair of switch button members electrically connected to the first conductive member, each of the first and second switch button members having a first switch setting and a second switch setting, each of the switch button members selectively contacting one of the printed circuit boards so that actuation of the first switch setting generates a first control signal and actuation of the second switch setting generates a second control signal.

18. The surgical instrument handpiece of claim 17, wherein the first control signal is delivered to a power source and causes the instrument to be actuated at maximum power, the second control signal being delivered to the power source and causing the instrument to be actuated at a minimum power.

19. The surgical instrument handpiece of claim 17, wherein the second conductive member comprises a conductive bore member extending through an outer shell of the switch end cap, the instrument being received within and extending through the bore member and the first conductive member further including a conductive ring member disposed between the conductive bore member and the outer shell.

20. The surgical instrument handpiece of claim 19, wherein the conductive ring member is coupled to a spacer member disposed about the conductive bore member so that the conductive ring member is electrically isolated from the conductive bore member.

21. The surgical instrument handpiece of claim 19, wherein the conductive bore member comprises a metal cylindrical tube.

22. The surgical instrument handpiece of claim 21, wherein the plurality of conductive fingers of the second conductive ring member act as a retention mechanism for detachably retaining the switch end cap to the handpiece body by being biased outwardly so that coupling between the switch end cap and the handpiece body causes the conductive fingers to flex inwardly against the outward bias force applied by the conductive fingers.

23. The surgical instrument handpiece of claim 19, wherein the conductive ring member includes a plurality of conductive fingers connected in an annular ring and disposed radially about the conductive bore member, the conductive fingers electrically contacting the handpiece body which acts as a conductive member so that a first electrical pathway from the cable is defined by the conductive handpiece body and the conductive ring member, whereby during rotation of the switch end cap, the conductive fingers travel radially in contact with the handpiece body.

24. The surgical instrument handpiece of claim 19, wherein the conductive bore member intimately contacts a plurality of conductive fingers which formed a part of the first conductive element and are electrically connected to the cable so that a second electrical pathway from the cable is defined by the conductive fingers of the handpiece body and the conductive bore member, whereby during rotation of the switch end cap, the conductive fingers travel radially in contact with conductive bore member.

25. The surgical instrument handpiece of claim 1, further comprising a seal member disposed within the switch end cap near the distal end thereof, the seal member sealingly engaging the blade so as to prevent foreign matter from entering and contacting the switch mechanism.

26. The surgical instrument handpiece of claim 25, wherein the seal member comprises a ring member.

27. The surgical instrument handpiece of claim 1, wherein the instrument is one of a surgical blade, scalpel, and shear instrument.

* * * * *